United States Patent
Geng

(10) Patent No.: US 9,566,537 B2
(45) Date of Patent: Feb. 14, 2017

(54) MULTIDIMENSIONAL LIQUID CHROMATOGRAPHY SEPARATION SYSTEM AND SEPARATION METHOD FOR PROTEIN SEPARATION

(71) Applicants: XI'AN AOLAN SCIENCE AND TECHNOLOGY CO., LTD., Xi'an (CN); NORTHWEST UNIVERSITY, Xi'an (CN)

(72) Inventor: Xindu Geng, Xi'an (CN)

(73) Assignees: XI'AN AOLAN SCIENCE AND TECHNOLOGY CO., LTD., Xi'an (CN); NORTHWEST UNIVERSITY, Xi'an (CN)

( * ) Notice: Subject to any disclaimer, the term of this patent is extended or adjusted under 35 U.S.C. 154(b) by 0 days.

(21) Appl. No.: 14/634,924

(22) Filed: Mar. 2, 2015

(65) Prior Publication Data
US 2015/0165343 A1    Jun. 18, 2015

Related U.S. Application Data

(63) Continuation-in-part of application No. PCT/CN2012/080868, filed on Aug. 31, 2012.

(51) Int. Cl.
| | |
|---|---|
| *B01D 15/18* | (2006.01) |
| *C07K 1/16* | (2006.01) |
| *B01D 15/30* | (2006.01) |
| *B01D 15/34* | (2006.01) |
| *B01D 15/42* | (2006.01) |
| *B01D 15/36* | (2006.01) |
| *G01N 30/46* | (2006.01) |
| *G01N 30/10* | (2006.01) |
| *G01N 30/20* | (2006.01) |
| *G01N 30/88* | (2006.01) |

(52) U.S. Cl.
CPC ......... *B01D 15/1878* (2013.01); *B01D 15/30* (2013.01); *B01D 15/34* (2013.01); *B01D 15/362* (2013.01); *B01D 15/424* (2013.01); *G01N 30/462* (2013.01); *G01N 30/463* (2013.01); *G01N 30/465* (2013.01); *C07K 1/16* (2013.01); *G01N 30/10* (2013.01); *G01N 30/20* (2013.01); *G01N 2030/8831* (2013.01)

(58) Field of Classification Search
None
See application file for complete search history.

(56) References Cited

PUBLICATIONS

Wehr, "Multidimensional Liquid Chromatography in Proteomic Studies," LC•GC Europe (2003) 2-8.*
Dugo et al., Journal of Chromatography A (2008) 1184, 353-368.*

* cited by examiner

*Primary Examiner* — Marcela M Cordero Garcia
*Assistant Examiner* — Catherine Mader
(74) *Attorney, Agent, or Firm* — Matthias Scholl, PC; Matthias Scholl

(57) ABSTRACT

A multidimensional liquid chromatography separation system has a mobile-phase storage tank, a first liquid transfer device, a second liquid transfer device, a first sample introduction device, a second sample introduction device, a separation device, a collection, storage device, at least two drainage devices and a flow path switching device. A separation method for protein separation using the multidimensional liquid chromatography separation system has the steps of: 1) preparation in advance, 2) the first dimensional separation, 3) collection and storage of the intermediate fraction, 4) the second dimensional or multidimensional separation and repeating the steps 3) and 4).

20 Claims, 6 Drawing Sheets

MULTIDIMENSIONAL LIQUID CHROMATOGRAPHY SEPARATION SYSTEM AND SEPARATION METHOD FOR PROTEIN SEPARATION

CROSS-REFERENCE TO RELATED APPLICATIONS

This application is a continuation-in-part of International Patent Application No. PCT/CN2012/080868 with an international filing date of Aug. 31, 2012, designating the United States, now pending. The contents of which are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to a multidimensional liquid chromatography separation systems for protein separation. In particular, a multidimensional liquid chromatography separation systems using for protein online quick separation is related. The separation method for protein separation using this liquid chromatography separation system is also provided in the present invention.

Description of the Related Art

Liquid chromatography is the most effective methods for analysis, separation and purification of protein, which is widely used in the extraction and separation of active protein from body fluid of natural plant and animal, and preparation and production of all kinds of recombinant protein drug in genetic engineering, and is also the essential equipment in the biochemistry laboratory, for example, protein and peptide separation in proteomics research in order to find the "mark" protein. Because the environment composition biological macromolecules exist is very complicated, it is often called the separation and analysis of biological macromolecules (biopolymers) in complicated components. Chromatographic column is the core of the chromatographic analysis. Scientists have been trying to improve the effect of chromatographic column so that the separation and analysis of general more complex materials can be done on a sample by a single chromatographic column. Chromatographic column is the core of the chromatographic analysis.

For the separation of small solutes, the number of theoretical plate (NTP) of liquid chromatographic column is generally for $10^4$-$10^5$. However, for the analysis of more complex mixture, such as component separation in cell, body fluids and tissue of animals, the resolution of conventionally chromatographic column by now is far less than demand, so two-dimensional liquid chromatography (2D-LC) or multidimensional liquid chromatography (mD-LC) must be used to partially solve these problems. The technology 2D-LC and mD-LC has become the research hotpoint and development direction of the modern chromatography in future.

For 2D-LC and mD-LC separation, there are two ways: off-line and on-line. 2D-LC separation in early stage mainly employs off-line method. The first dimensional separation is collected by hands, and then the fraction is injected into the second dimensional chromatographic column for separation. If the collected fraction is directly injected into the second column, the sampling amount must be a very small part of the fraction. If whole or most of the collected fraction is required to inject into the second column, the collected fraction must be pre-treated (concentration, buffer exchange). Off-line method has shortcomings, such as time-consuming, difficult to operate, sample contamination easily, low recovery and poor repeatability etc.

To satisfy the request of 2D-LC and mD-LC methods, several companies have been exploring the on-line method accompanying with producing several liquid chromatographs. However, from the standpoint of principle, these chromatographs are only improved based on the conventional chromatograph, and a set of chromatographic column (2-3 pieces) are inserted in parallel manner, as well as switch interfaces between these parallel chromatographic columns assembled, so as to transporting the fraction from one of the chromatographic columns to another for the separation of next mode by on-line manner. There are many problems existing in these on-line 2D-LC and mD-LC methods, such as the problem of mobile phase compatibility should be solved between different patterns of chromatography combination and the required interface is also a key technical problem.

Switch interface is the key device to the whole system of mD-LC technique. Commonly used ones are sample loops storing and transferring samples alternately, parallel columns enriching analytic samples alternately, capture column enriching samples, as well integrated two chromatographic columns with no interface. However, these instruments all have fatal flaw. On-line 2D-LC and mD-LC liquid chromatograph with interfaces can only inject 1-10% of the samples (only a few microliter) collected in the first dimension to the second dimensional chromatographic separation. In addition, it can be not used for protein separation in preparation scale, especially in industrialization production scale; As for mixed-mode chromatographic column without interfaces, two kinds of mobile phases must be completely compatible. Only in some specific circumstances, such as strong cation exchange chromatography (SCX) packing material being the first dimension and reversed phase liquid chromatography (RPLC) packing material being the second dimension, can such on-line two-dimensional separation be done. If the packing materials are packed on the contrary, this no switcher method will be useless.

Based on the background of this scientific development, scientists put forward the method of "mixed-mode chromatography (MMC). MMC is a type of chromatographic method in which multiple interaction modes take place between the stationary phase and solutes in the feed. This method has higher selectivity and high chromatographic column load, which provides selections and ideas for the development of semi-preparation and the preparation chromatography. However, in comparing with the traditional chromatographic column with the separation mode controlled by only one kind of force, MMC is controlled mainly by one kind of the two forces and the other one is the auxiliary, thus it only plays a role of improving the main separation mode. As a result, it is still employed for "one column-one usefulness".

As early as in the 80s, Guiochon et al. (Chromatographia, 17 (3), 124-121, 1983) have put forward the method of 2D-LC with two dimensional chromatographic columns. The two-dimensional here refers to is the two-dimensional (plane) chromatography in space and the two-dimensional chromatographic column is for square (10 cm×10 cm), just as the conventional thin-layer chromatography plate. They applied for a patent, but didn't get it promoted and it has not been found any application in literature. Generally speaking, what we use in two-dimensional chromatography is the cylindrical chromatographic column. Two years ago, the patent applicant et al. put forward the "on-line two-dimensional liquid chromatography of protein separation with a single-column", using the cylindrical two-dimensional chromatographic column. Several valves and spiral sample loops are inserted into the conventional liquid chromatograph, and then, with a cylindrical two-dimensional chromatography column, we carried out the fast 2D-LC separation of proteins. However, there are still problems existing of this method: (1) The maximum flow rate of the chromatograph is limited to 5 mL/min and the maximum volume of the sample loop of the collect-reserve device is only 5 mL, its can only operate on the analysis scale and can be not applied to preparative and productive scales; (2) This instrument is set for protein separation with one chromatographic column, therefore, it can be not employed to approach to the goal to obtain target protein with high purity which can only be carried out by means of mD-LC method using several types of chromatographic columns (such as the purity of insulin injections for protein >99%); (3) There is no strong theoretical support to design a multi-dimensional chromatograph and can only manual operate relying on experience. We neither can design software which is necessary to control modern instruments. What's more, this method can not be applied for polypeptide separation at that time; (4) All the chromatographic columns are specially made for "2D-LC" and there is no commercial products, so it is difficult to be employed by other chromatographers; (5) More importantly, there are only several equipment accessories patching up disordered on the conventional liquid chromatograph which is only employed to support the possibility for establishing this method. There is no whole idea of the framework on manufacturing equipment, technical scheme or technical parameters on how this method can carry out. There are more advantages that the 2D-LC is implemented using cylindrical 2D chromatography columns (simply called it as 2D column) than the flat form 2D chromatography columns.

Even so, there are several potential advantages of this chromatography: All operations of 2D-LC analysis for protein, including the collection and storage of the fractions from the effluent of the first separation model, the on-line buffer exchange under a high flow rate, the re-equilibrium of the chromatographic system, the on-line re-injection of the samples back to the same 2D column to carry out the second dimensional separation, are all accomplished in a closed system, so as to realize the "on-line two-dimensional chromatogram rapid analysis for proteins with a single-column". This system has features that not only can prevent from the environmental pollution, but also can make the target protein be quantitatively transported to the second dimension chromatographic separation. Therefore, the detection limit and sensitivity of low abundance functional protein in proteomics can be improved 10-100 times, which will greatly accelerate the speed of "top-down-mass spectrometry" strategy in proteomics. If using the MMC mixed mode column, as its column loading is much higher than conventional chromatographic column, it can greatly save cost in the production of protein drugs in large scale.

Considering the potential advantages of this method, the applicant explores an equipment using for protein separation "protein multidimensional liquid chromatography purification system".

SUMMARY OF THE INVENTION

In view of the above-described problems, it is one objective of the invention to provide a multidimensional liquid chromatographic separation system and a method for separation and purification of proteins and peptides using this system, which can carry out the separation, rapid analysis and large-scale preparation of peptides and proteins (hereinafter referred to as protein) by means of on-line manner, so as to shorten the purification technology, increase the separation speed and the recovery of target products during the process of the two-dimensional and multi-dimensional separation, prevent from the contaminations from the environment, reduce the time and cost of separation process.

The applicant has discovered that, in the four kinds of liquid chromatographic mode reversed-phase liquid chromatography (RPLC), hydrophobic interaction chromatography (HIC), affinity chromatography (AFC) and ion exchange chromatography (IEC), on the condition that proteins are separated by linear gradient elution, there is a universal phenomenon that the retention behavior of proteins in chromatographic column is "steady-migration charater", and each protein has its own unique "steady-migration" area or time space. In other words, when elution concentration of the mobile phase is lower than the protein critical migration concentration ($C_{CMP}$), the protein will migrate on the column bed. With the eluent concentration increasing gradually to $C_{CMP}$, proteins will moved and eluted out column with one by one manner according to their respective "steady-migration" space. The retention time corresponding to the critical migration elution concentration $C_{CMP}$ is called the critical migration time $t_{CMP}$. Therefore, the time space from the beginning (t=0) to the $t_{CMP}$ of the gradient time, provides an auxiliary operation space for various chromatographic separations for protein separation and purification. As long as the linear gradient elution conditions remain unchanged and the eluent concentration of the displacer of the mobile phase in the column is lower than $C_{CMP}$, the retention time of proteins will remain unchanged.

Hereinafter, FIG. 1 is illustrated as an example to explain the protein "steady-migration" phenomenon:

What is used in FIG. 1 is a cake-shaped column, also known as the chromatographic cake, with a length of 1 mm and a diameter of 10 mm. FIGS. 1A, 1B and 1C, are respectively the chromatograms of benzyl alcohol, carbonic anhydrase enzyme and a 15-peptide (GEPPPGKPADD-AGLV) (SEQ ID NO: 1) under the condition of asynchronous injection in RPLC linear gradient elution. FIG. 1D, FIGS. 1E and 1F are respectively the relationship between retention time and the asynchronous injection time of benzyl alcohol, carbonic anhydrase and the 15-peptide (SEQ ID NO: 1). Chromatographic conditions: chromatographic cake (10 mm×1 mm inner diameter); the RPLC packing materials (particle diameter of 3 μm, pore size 30 nm); mobile phase of acetonitrile-water (0.1% trifluoroacetic acid).

Under the condition of RPLC linear gradient elution (eluent for acetonitrile-water solution), respectively, the asynchronous injection (That is to say, the sample is injected respectively after a certain time interval (FIG. 1 for 1 minute) after the beginning of the gradient. In other words, the sample is injected in different elute concentration for liquid chromatographic separation of small molecule solute benzyl alcohol, biological macromolecules carbonic anhydrase and the 15-peptide (SEQ ID NO: 1). The chromatograms obtained are respectively shown in FIG. 1A, FIG. 1B and FIG. 1C. Drawing pictures with the retention time $t_R$ of the three samples as the y-coordinate, linear gradient time t as the primary x-coordinate and the eluent concentration $C_{MeCN}$ as the secondary x-coordinate, the retention behavior curves are shown in FIG. 1D, FIG. 1E and FIG. 1F. We can see from the FIGS that, benzyl alcohol, as a small molecule compounds and carbonic anhydrase, as a biological macromolecules and the 15-peptide (SEQ ID NO: 1) as a polypeptide show two different retention behaviors. The retention behavior curves of carbonic anhydrase and the 15-peptide (SEQ ID NO: 1) have obvious horizontal linear part and rising part and there are obvious turning points between the two parts and the turning points are marked in FIGS. 1D and 1E with arrows. We called it as "critical migration point" and the abscissas numerical it corresponds are respectively the "critical migration time $t_{CMP}$" and "critical migration eluent concentration $C_{CMP}$" of carbonic anhydrase and the 15-peptide (SEQ ID NO: 1) in RPLC mode. When the time $t_I$ that sample injection lags behind gradient time is less than $t_{CMP}$ (i.e., when the concentration of eluent acetonitrile is below $C_{CMP}$), carbonic anhydrase and the 15-peptide (SEQ ID NO: 1) cannot start to migrate and definitely can be not eluted out; and when the time $t_I$ that sample injection lags behind gradient time is more than $t_{CMP}$ (i.e., when the concentration of eluent acetonitrile is greater than $C_{CMP}$), carbonic anhydrase and the 15-peptide (SEQ ID NO: 1) can start to migrate and finally to be eluted from columns with continuous gradient elution. That is the "steady-migration charater" that protein and polypeptide show on chromatographic cake, or column. It's the discovery of this "steady-migration" that protein and polypeptide show on chromatographic cake, or column that lays on a theoretical foundation for the rapid and efficient separation of proteins and peptides on such a thin chromatographic cake.

According to the findings above, applicant puts forward a type of multidimensional liquid chromatograph separation system and the method of using this system for protein separation.

To achieve the above objective, in accordance with one embodiment of the invention, there is provided a mD-LC instrument separation system for protein separation, which includes a detection device, in which the mD-LC separation system includes:

(1) the mobile phase tank, used for the storage of mobile phase for multi-dimensional liquid chromatography separation;

(2) the first and second infusion device, the first and second infusion device works independently. They get mobile phase which is suitable for the liquid chromatography separation from the mobile phase tank and then, the mobile phase transfers to the multi-dimensional liquid chromatograph separation system flow path. They can also measure and adjust their flow independently;

(3) the first and second injector device, the second sample injection device includes a sample mixer; wherein, the first sample injection device uses a six injection valve for original sample injection; and the second sample injection device is used in two-dimensional and multi-dimensional chromatography purification process;

(4) the separation device, which includes chromatographic column switching unit and 'n' chromatographic columns, or 'q' chromatographic column with a total number of separation modes 'm'. Wherein, the chromatographic column switching unit helps to put the liquid in the separation device selectively into one of the chromatographic column of the 'n' chromatographic columns. The number 'n' is a nonnegative integer and 'm' is number of different separation modes used in the multi-dimensional liquid chromatograph separation system mentioned, and 'n' and 'm' must satisfy as that:

$$m \geq n \quad (1)$$

When m (m≥2) mode separation is achieved by using 'q' mixed mode chromatographic column, $$n = m - q \times (i-1) \quad (2)$$

wherein, the subscript 'i' is a positive integer; 'qi' stands for the number of chromatographic columns having 1' separation model;

(5) the collect-reserve device, which includes "p" sample loops switching units and "p" is greater than or equal to 1. The collect-reserve device helps to control the liquid in the collect-reserve device to pass flow into at least one of the collect-reserve device selectively;

(6) at least two draining devices, the liquid of mD-LC separation system will be discharged outside the system through the draining device mentioned;

wherein, the draining holes of the six-way injection valve using as the first injection device can be used as the first discharge device of the multi-dimensional liquid chromatograph separation system; At the same time, the second draining device can be used to collect fractions, as well as discharge waste;

(7) the flow path switching device is made up from valves connected to the device above and pipes. By switching the valves of the flow path switching device, not only the flow path for conventional liquid chromatography separation but also the flow path for md-LC separation can be formed;

wherein, in the first dimensional separation, the first infusion device will transport the mobile phase for the first dimensional separation to the first sample injection device. The first sample injection device is employed for the original protein sampling from outside the system, and then, the samples flow together with mobile phase from the first infusion devices into the separation device. The samples are separated as the first dimensional separation through the separation device and different fractions are obtained.

During each dimensional separation, different intermediate fractions required to be separated further is collected through the collect-reserve device after separation. These intermediate fractions are stored in at least one of the sample loops and those does not need to be separated further are discharged from the system through the draining device.

In two-dimensional or multi-dimensional separation, mobile phase having suitable composition for liquid chromatographic separation are transported by the first infusion device to the collect-reserve device, and then, all or part of the intermediate fractions stored in at least one of the sample loops flow together with the mobile phase into the injection mixer; mobile phase having suitable composition for liquid chromatographic separation are transported by the second infusion device to the injection mixer too. The injection mixer helps to mix all or part of the intermediate fractions with the mobile phase from the second infusion device and the second dimensional injection mixture with suitable composition is formed. And then, the second or multi-dimensional liquid chromatograph separation is done for the injection mixture and different two dimensional fractions are obtained.

Wherein, the first and second infusion devices can adjust and measure the flow amount of the mobile phase with suitable concentration they transport for two-dimensional or more multi-dimensional separation, so that the eluent concentration of injection mixture for two-dimensional or more multi-dimensional separation is lower than the critical migration eluent concentration of intermediate fractions in the injection mixture that need to retard for the second or multi-dimensional separation.

When chromatographic system periodically, strong eluent can be connected to any piping and equipment. For example, if the chromatographic system or part of the separation device needs periodically cleaning, the first and second infusion system can transport any elution solvent.

In a class of this embodiment, "proteins" includes protein, synthetic polypeptides and the polypeptides from protein digestion; "protein sample" or "original samples" refers to the mixture containing both proteins and peptides.

In a class of this embodiment, "separation" refers to the liquid chromatographic separation.

In a class of this embodiment, "separation mode" of liquid chromatography is synonymous with the "separation mechanism".

In a class of this embodiment, "dimension number" of liquid chromatographic separation refers to the number of separation modes using cylindrical chromatographic column to accomplish liquid chromatographic separation during liquid chromatographic separation process (i.e., the number of separation in different separation modes after samples to be separated with the cylindrical liquid chromatographic column). "Multi-dimensional liquid chromatography" means liquid chromatography including two-dimensional liquid chromatography or more than two dimensions, (such as three-dimension liquid chromatography). In other words, the mD-LC also includes 2D-LC.

In a class of this embodiment, "column" refers to cylindrical liquid chromatography column (column for short), "chromatographic column having "i" separation modes" refers to chromatographic column which has a separation modes "i" and can be used in "i" different kinds of separation process. The technicians in this field are easy to understand, when "i"=1, the chromatographic column have only one HPLC separation mode, which can be used in only one chromatographic column separation process (called "one-dimensional chromatography column" in the invention); When "i" ≥2 or higher, the chromatographic column has two or more liquid chromatographic separation modes, which can be used in two or more different modes with a single chromatographic column (called "mixed mode, or mixed mode chromatographic (MMC) column" in the invention). Under rare cases, such as separation of peptides with RPLC, it also can be used to implement a single model of two-dimensional chromatographic separation.

In a class of this embodiment, as is well known, "fraction" refers to the part of the mobile phase containing the target products which has different retention time from other components after chromatographic separation. "Intermediate fraction" refers to the target product fraction, which are achieved from the previously dimensional separation and required to be separated with other separation mode.

In a class of this embodiment, "mobile phase suitable for the liquid chromatographic separation" means that this mobile phase can be used as mobile phase of a specific dimensional liquid chromatography separation and the target protein can be separated well with the mobile phase. For the field technician, it is known by everyone that how to determine the suitable mobile phase basing on the nature of the isolated target protein, the selected chromatographic separation principle and used types of the chromatographic column.

In terms of handle protein mass, multi-dimensional liquid chromatograph separation system in the present invention can be divided into for analytical scale to be less than 10 mg, semi-preparative scale to cover from 10 mg to 100 mg and preparative scale to range from 100 mg to 100 g and productive purposes to be greater than 100 g. Technicians in this field are easy to understand, each device of mD-LC separation system of different purpose as mentioned above has different sizes. In terms of mD-LC separation systems of preparative and productive types, term "sample injection" in this patent can be interpreted as "sampling", "material injection"; "sample" can be interpreted as "raw material", "product" can be interpreted as "goods".

Mobile Phase Tank

The mobile phase tank for mobile phase reservoir is well-known by technicians in this field. Technicians in this field can understand easily that the number of mobile phase tank bases on the types and scales of mobile phase using in this mD-LC separation system. Compared to conventional liquid chromatography separation system, the number of the employed mobile phase in liquid chromatography separation system of this patent is more, thus more mobile phase tanks are needed. For example, two-dimensional liquid chromatography separation system based on this invention needs to use ≥4 different kinds of mobile phase and 4 mobile phase tanks are required; three-dimensional liquid chromatography separation system based on this invention needs to use 5 or more different kinds of mobile phase and 5 mobile phase tanks are needed. As shown in FIG. 2, the two infusion systems can connect with four mobile phase tanks respectively and is totally 8 mobile phase tanks. Preferably, the 2D-LC and mD-LC liquid chromatography separation system based on this invention include at least four mobile phase tanks. From analytical scale to semi-preparation and to preparation scales, and then, to productive scale, mobile phase tank change respectively from glass bottles with 1 L volume to stainless steel storage tank with volume of several tons. For large-scale and fixed product, because of fixed production technology, the number of storage tank can be greatly reduced.

Infusion Device and Injection Device

The first infusion devices and the second infusion device include one or more pumps, such as syringe metering pump, reciprocating metering pump and diaphragm metering pump.

Optionally, the first infusion devices and the second infusion device have multivariate gradient units and pumps, respectively. The multivariate gradient units consist of multiple infusion channels and can transport and measure the flow amount of any channel. The multivariate gradient unit is well-known by technicians in this field and preferably, each of the infusion devices has at least four channels.

Optionally, the first infusion devices and the second infusion device are first pump and second pump, respectively, with multiple infusion channels and can transport and measure the flow quantity of any channel and preferably, the first pump and second pumps are, respectively, pumps with at least four channels.

Technicians in this field are easy to determine the model of the pumps above and which kind of injection should be used, manual injector or auto-sampler, according to the injection pressure, flow rate and pumping accuracy of the mD-LC system. Optionally, the pumps are high pressure pumps with large capacity which are well-known by technicians in this field. It is more prefer to use diaphragm high pressure pump or reciprocating high pressure pump by the technicians in this field.

For mD-LC separation system of analytical type, the high pressure pump refers preferably to ultra-high pressure pump with which liquid can be pressurized to less than 40 Mpa or more than 40 Mpa. For multidimensional liquid chromatography separation system of preparative and productive scales, the high pressure pump refers preferably to high-pressure pump with which liquid can be pressurized to more than 20 Mpa.

The multidimensional liquid chromatography system is integrated type. All hardware are assembled in a shell and operated through one control system; Or the multidimensional liquid chromatography system is separated type, namely that each hardware and automatic control system is assembled in two or more shells and operated using the automatic control system of the existing chromatograph or other automatic control systems.

For analytic multidimensional liquid chromatography separation system, the high-pressure pump has optimized flow rate ranging from 0.001 to 10 mL/min; for preparative multidimensional liquid chromatography separation system, the high-pressure pump has optimized flow rate ranging from 0.01 to 100 mL/min; for productive multidimensional liquid chromatography separation system, the high-pressure pump mentioned has optimized flow rate ranging from 0.1 to 10 L/min.

Preferably, the infusion device also includes degassing unit and the degassing unit removes gas in the mentioned mobile phase with a well-known way.

Optionally, there are tank valves between the mobile phase tank and said infusion device. The tank valves are used to control whether the mobile phase tank and the infusion device are connected or not.

Preferably, the total mobile phase flow that the first infusion device and the second infusion device in this mD-LC separation system can transported is more than the mobile phase flow that was transported by a conventional single infusion device on the gradient elution of liquid chromatography separation.

The injection mixer of the second injection device is mixer which is well-known by technician.

The injection device is injector which is well-known by technicians in this field and is widely used in conventional liquid chromatography separation system. The injector can be manual injector or auto-sampler, chromatographic pump. For example, the injector can be a conventional 6-port chromatography injection valve and samples to be separated can be injected quantitatively into the multidimensional liquid chromatography separation system in this patent.

The injection mixer of the second injection device is mixer which is well-known by technician in this field and any mixer which is suitable for mixing intermediate fractions and mobile in the conventional liquid chromatography system can be used. Optionally, the injection mixer includes but not only mixing tank and mixer.

The mixing tank includes a stirrer. Examples of the stirrer include but not limited to magnetic stirrer or stirring blade driven by motor or engineer.

Examples of the pipeline mixer includes but not limited to nozzle pipeline mixer, vortex pipeline mixer, porous plate pipeline mixer, profiled plate pipeline mixer, static pipeline mixer.

Optionally, there is a valve on the pipeline connecting the mentioned second injection device and the mentioned second infusion device.

For the next dimensional separation, as mentioned above, before feeding the target product which includes intermediate fraction and flows from the collect-reserve device and has been separated in the last dimensional chromatography into the separation device by the second injector device, all or parts of the collection liquid of the last dimension intermediate fraction, pushing by the first infusion device, must be adjusted and measured with the mobile phase rate transported by the second infusion device, so that the final eluent concentration of the mixture which we can call "diluent of the intermediate fraction containing the target products" or "target products reinjection solution" is lower than the critical migration eluent concentration of the target products. Technicians in this field should be able to understand that it's necessary for the achievement of the second or multi-dimensional separation that the "pretreatment" ("buffer exchange" of the sample to prevent the quality of the samples and volume overloading) of the fractions from the last dimension and to be separated in the next dimension must be done. In other words, it is because infusion device and injection device based on this invention can mix the intermediate fraction with mobile phase in a specific way so that eluent concentration after mixing is lower than the critical migration eluent concentration of proteins, that makes it possible for the multi-dimensional liquid chromatography separation system based on this invention to achieve the target protein multi-dimensional liquid chromatography separation.

To carry out the special mixing way, firstly, we should pay an attention to that, the critical migration eluent concentration of some target protein is determined based on the liquid chromatography separation condition, which includes the kinds of the mobile phase solution, separation modes and the characteristics of chromatographic column, so that the special critical migration "eluent concentration" of the protein under this separation condition is required to determine. The corresponding eluent refers especially to the mobile phase or displacer as strong eluent solution in the next dimensional separation and the concentration of mobile phase or displacer is the critical migration concentration of the protein under this separation. Accordingly, for the sample mixture, the eluent solution which referred to in the eluent concentration is the mobile phase solvent or displacer as strong eluent solution in the next chromatographic separation.

Secondly, because that the critical migration eluent concentration of some proteins is specially corresponding to the nature of the protein itself, the kinds of the employed mobile phase solution and the selected chromatographic column, all the critical migration eluent concentration of proteins need to be employed in 2D or more multi-dimensional separation shall be determined by experimental method in advance.

For example, the critical migration eluent concentration can be determined in advance by using the corresponding pure protein samples under the same separation conditions, or linear gradient elution separation under the conditions of asynchronous sampling with mixture contains the corresponding protein. Technicians in this field should be able to understand that once the critical migration eluent concentration of certain proteins under certain conditions is predetermined, then the critical migration eluent concentration can be used in the separation process under the same separation conditions, having no need to determine the critical migration eluent concentration again.

By reading the instructions above, technicians in this field should be able to adjust and measure the liquid amount transported by the first and second infusion device, so that the eluent concentration of the sample mixture is lower than the critical migration eluent concentration of all the proteins need to be retained in this dimensional separation.

Separation Device

The chromatographic column or chromatographic cake of the separation device can be any of the chromatographic column or chromatographic cake known by technicians in this field using for protein separation. According to the common sense known by technicians in this field, for different protein samples to be separated, the technicians in this field can easily choose the appropriate chromatographic column or chromatographic cake for protein separation.

In this patent, the "suitable" chromatographic column or chromatographic cake refers to that the chromatographic column has the desired liquid chromatographic separation mode, and can at least separate partially the proteins entering into the column.

When the chromatographic column or chromatographic cake is under the same handling sample size, the column pressure drop of the chromatographic cake is lower than that of the common chromatographic column's, therefore, it's more suitable to use on high velocity and low pressure conditions for the multidimensional liquid chromatography separation system in preparative or productive scales.

In this patent, the multi-port valve refers to valves with hole-number equal to or more than 8, such as 10-way valve, or more-channel valve.

Those skilled in this field can understand easily that if the separation system includes more than two chromatographic columns, the suitable chromatographic column is connected to the flow path selectively through the switching valve rather than the special switching device in conventional multi-dimensional chromatography.

If the separation system includes more than two chromatographic columns or cakes, the chromatographic column or cake switching unit of the separation system can includes at least one multi-port valve. The multi-port valve has a valve inlet as the inlet of the separation device and n valve outlets connecting with the n chromatographic columns one-by-one. The multi-port valve helps to transport the liquid in the separation device selectively into one of the chromatographic columns or cakes by switching the n valve outlets.

Preferably, the chromatographic column or cake switching valve of the separation includes the first and second multi-ported valve. The first multi-port valve has a valve inlet as the inlet of the separation device and n valve outlets connecting to the n chromatographic columns one-by-one. The second multi-port valve has a valve outlet as the outlet of the separation device and n valve inlets connecting with the n chromatographic columns one-by-one. By switching the n valve outlets of the first multi-port valve and the n valve inlets of the mentioned second multi-port valve, one of the chromatographic columns or cakes is connected, that is to say, the liquid flowing into the separation device passes through the first multi-port valve and flows into the chromatographic column, and then, flows out of the separation device through the second multi-ported valve.

It should be pay an attention that the liquid chromatography separation mode using in each dimension can be the same or different, therefore, the separation mode number 'in' using in the mD-LC separation system can be equal to or smaller than the separation times of this mD-LC separation system. Preferably, this two-dimensional separation mode number is the chromatographic column number q in "orthogonal-type" mode and the column number can be replaced by the same with the 2D-LC column switching valve with a single column. Of course, in general the adjacent two-dimensional separation modes are usually different.

Technicians in this field can understand easily that if there is only one column in this said separation system there will be no switching valves between the chromatographic columns.

Preferably, the mD-LC system based on the present invention includes desalination device. The desalination device used in liquid chromatography system is well-known by technicians in this field and it helps to remove at least part of the salt from the liquid. For example, the conventional desalination device can be a size exclusion column parallel with the column of the separation device to desalt.

Detection Device

The detection device includes any detectors using in liquid chromatographic method for the different protein components detection. The detector can be any type of detectors commonly used in the liquid chromatography system, which is well-known by technical personal in this field. Preferably, in the production scale process, mobile phase has high flow rate, therefore, a liquid discharge hole in parallel with the detector must be added to discharge, detect and collect the target product from the discharge hole simultaneously. $1/10$ or $1/1000$ of the liquid flowing into the detection device is separated and then send into the detector.

Collect-Reserve Device

The sample loops of the collect-reserve device can be liquid storage tube, liquid storage tank, reservoir or mutual series of liquid storage tube and/or liquid storage tank and/or liquid storage tank. The number of the sample loops "p" depends on the complexity of the protein sample to be separated and is also related to the fraction number which collected and stored from the last dimensional separation and to be separated in next dimensional separation. Preferably, "p" meets that:

$$p \geq \mathrm{Max}(x_j) \qquad (3)$$

wherein, '$x_j$' is the intermediate fraction number that collected and stored in the j dimensional separation and to be separated further.

Optionally, the geometry volume of the sample loops are all or partial different from each other. Technicians in this field can understand easily that larger volume fractions can be reserved in larger sample loops and smaller volume fractions can be reserved in smaller sample loops and one fraction also can be reserved in two or more sample loops.

Preferably, except for the 'p' sample loops satisfying the formula (3), the collect-reserve device still include a small volume sample loop. The small volume sample loop is used to discharge fractions no need to collect and reserve from the discharge hole of the collection and liquid reserve device quickly.

Preferably, the sample loop switching unit of the collect-reserve device includes the third multi-port valve (as shown in FIG. 2, one of 11-1) and the fourth multi-port valve (as shown in FIG. 2, one of 11-2). The third multi-port valve has a valve inlet as the inlet of the liquid reserve device and 'p' valve outlets connecting with the 'p' chromatographic columns one-by-one. The fourth multi-port valve has a valve outlet as the outlet of the liquid reserve device and 'p' valve inlets connecting with the p chromatographic columns one-by-one. By switching the 'p' valve outlets of the third multi-port valve and the 'p' valve inlets of the fourth multi-port valve, at least one of the sample loops is connected, that is to say, the liquid flowing into the collection and storage device passes through the third multi-port valve and flows into at least one of the sample loops, and then, flows out of the collect-reserve device through the fourth multi-ported valve.

More preferably, liquid are allowed to flow reversely through the third and fourth multi-port valve. That is to say, liquid are allowed to flow from the valve outlet into the valve inlet. At this time, by switching the p valve outlet of the third multi-port valve and the p valve inlet of the fourth multi-port valve, at least one of the collect-reserve devices is connected. Liquid into the collect-reserve device can flow into at least one of the collect-reserve device through the third multi-port valve and flow out of the collect-reserve device through the fourth multi-port valve. Liquid into the collect-reserve device can also flow reversely through the fourth multi-port valve into at least one device collection of the at least two collect-reserve device (i.e. flow from the fourth multi-port valve outlet and flow into the collect-reserve device through the fourth multi-port valve inlet), and then, flow reversely through the third multi-port valve out of the collection and storage device (i.e. flow from the third multi-port valve outlet and flow out of the collect-reserve device through the third multi-port valve inlet).

When removing salt with the SEC mode, because of the large amount of the liquid from the two dimension and the target protein concentration constant changing with time, what's more, it's impossible to inject all the sample completely into the SEC column for once, therefore, the collect-reserve device is oval and accompanied by using oscillator stirring to mix the collected liquid, the mixture is divided in to many parts and injected equivalently into the SEC column to remove salt.

Draining Device

The draining device is the conventional liquid chromatography system draining device which is well-known by technicians in this field. Liquid discharged out of the system through the draining device includes final separated product fraction which has no need to separate again and the waste in the flow path. As a simple case, the draining device can be tubing connecting to the outside of the system.

Preferably, the liquid chromatography separation system based on this invention includes the first draining device and the second draining device. The first draining device can discharge liquid waste from the detection device outside system; the second draining device can discharge liquid waste from liquid-reserve device outside the system, so that the first draining device can discharge the mobile phase displaced during injection and the second draining device can discharge the target product and waste.

Preferably, when the liquid chromatographic separation system based on this invention is preparative or productive scale, large amount liquid is not allowed to flow through the detector cell, so a third draining device is set up. The third draining device setting parallel with the detector is a branch pipe with a diameter far more than the detector cell. It receives mobile phase from the separation device so that more than 90% of the mobile phase can be discharged from the third draining device.

Optionally, the draining device can be the three draining devices commonly used in liquid chromatography system, which is well-known by technician in this field. The first draining device discharges mobile phase replaced during samples injection; the second draining device is the outlet of target products and large amount of waste liquid; and the third draining device is specially designed for mass production. By connecting a two-port valve in parallel with the detector and adjusting the hole size of the two-port valve, 90% to 99.9% of the mobile phase containing the target products discharges out of the product collection device or waste collection device without getting through the detector and only 0.1% to 10% of the same mobile phase flow synchronously into the detector.

Flow Path Switching Device

Preferably, the flow path switching device can constitute any kind of the following flow path selectively to switch flow path:

Conventional separation flow path, the mobile phase tank, first infusion device, first injector device, separation device, detection device and the first and second draining device are connected in turn in this flow path;

The first dimensional separation flow path, the mobile phase tank, first infusion device, separation device, detection device, collect-reserve device and the second draining device are connected in turn in this flow path;

The second or higher dimension separation flow path for intermediate fraction collection, the mobile phase tank, first infusion device, collection and storage device, second injector device, separation device, collect-reserve device, collection and storage device and second draining device are connected in turn. What's more, the mobile phase tank, second infusion devices and second injection device are connected in turn in this flow path;

The second or higher dimension separation flow path without collecting intermediate fraction, the mobile phase tank, first infusion device, collection and storage device, second injector device, separation device, detection device and the second draining device are connected in turn. What's more, the mobile phase tank, second infusion device and second injection device are connected in turn in this flow path;

In a class of this embodiment, each part's "connection one by one" in the flow path refers to that the sequence of each device is connected one by one trough valves and pipelines in the space and the fluid in the flow path flows sequentially in time through each of the adjacent components, so that liquid in the separation system based on the present mD-LC invention can flows through each part of the parts sequence according to sequence number. For brevity, there is no valve and pipeline listed specifically in the parts sequence.

Constant Temperature Device

Preferably, to prevent the loss of bioactivity of the separated protein during separation process, the mD-LC separation system based on this invention includes constant temperature device. The brevity constant temperature device keeps at least the brevity collect-reserve device remains constant temperature on which the inactivation time of proteins can extend. Optionally, the brevity constant temperature device keeps the entire mD-LC separation system based on this invention remain constant temperature on which the inactivation time of proteins can extend. The constant temperature is preferably 4° C. For example, the brevity constant temperature device can be constant temperature tank which is equipped with a cooling means, so that the space inside can stay at a constant temperature (preferably kept at 4° C.). At the same time, the collect-reserve device or the entire multi-dimensional liquid chromatographic separation system are accommodated in this space.

The constant temperature device can be assembled whole or partly with other parts of the chromatograph into a shell and to be a whole system. It also can be installed separately as an independent system.

Sterilization Device

Preferably, the multi-dimensional liquid chromatography separation system based on this invention includes the sterilization device. This sterilization device kills at least the bacterial in the collect-reserve device in a well-known manner. Optionally, the sterilization device kills at least partly of the bacterial in the mD-LC separation system based on this invention. The sterilization device includes steam generator device and steam entering device or electric heating device. The steam generator device can produce steam with a temperature of more than 140° C. and the steam entering device pushes the steam into the collect-reserve device of the multi-dimensional liquid chromatography separation system.

The sterilization device includes electric heating device which is heated through the electric power directly, or the hot air generating from the electric heating.

The sterilization device can be assembled all or partly with other parts of the chromatograph into a shell and to be a whole systems. It also can be installed separately as an independent system.

Automatic Control Device

Preferably, to achieve automatic operation, the multi-dimensional liquid chromatography separation system based on this invention includes automatic control device. This automatic control device can not only accomplish the conventional liquid chromatography automatic operation but also the automatic switching of the valves in the separation device, collection and storage device and flow path switching device. The mD-LC separation system based on this invention can be integral-type or separate-type differently. This automatic control device is as a whole and it can also divide into two independent control devices, the former as a "system" and the latter as automatic control system working together with the conventional liquid chromatograph.

Optionally, the mD-LC separation system based on this invention can also include conventional liquid mixing device. This conventional liquid mixing device is well-known by technical personal in this field and it helps to fully mix various components of the flow path with each other in a well-known manner. For example, this conventional liquid mixing device can be disposed after the infusion device, so that all kind of mobile phase liquid from the infusion device can mixed with each other better.

Shell

Optionally, part or all of the components of the mD-LC separation system based on this invention can be assembled in one or more shells, thereby forming integral-type or separate-type equipment. For example, the infusion device, injector device, separation device, collecti-reserve device, flow path switching device, automatic control device, conventional detection device and the conventional draining device can be assembled inside of one shell, thereby forming a multi-dimensional liquid chromatography of integrate-type and it also can be assembled in more than two shells, thereby forming a "system" of separate-type.

Two-Dimensional Liquid Chromatography Separation System

In particular, a 2D-LC separation system with a cylindrical chromatographic column using for protein separation (herein after referred to as 2D-LC separation system) is provided in this patent. This 2D-LC separation system includes detection device, its feathers are that said 2D-LC separation system includes:

1) mobile phase tank, using for the reserving mobile phase for two-dimensional liquid chromatography separation;

2) the first and second infusion device, which works independently. They get mobile phase which is suitable for the liquid chromatography separation from the mobile phase tank and then, the mobile phase is transported to the two-dimensional liquid chromatography separation system flow path. They can also measure and adjust their flow quantity independently;

3) the first and second injector device, the second injection device includes sample mixer;

4) separation device. It includes chromatographic column switching unit and 'n' chromatographic columns, or a chromatographic column with a total number of two separation modes. Wherein, the chromatographic column switching valve helps to put the liquid having been in the separation device selectively into one of the chromatographic column of the 'n' chromatographic columns. 'n' is a nonnegative integer 'n' meets that:

$$n > q \quad (4)$$

When two conventional single-mode chromatographic columns are used to achieve off-line 2D-LC on this multi-dimensional liquid chromatography separation system, n=2, q=0, m=2; it should be noted that, what described here is that how to achieve off-line and on-line 2D-LC on this multi-dimensional liquid chromatography separation system with conventional chromatographic columns (That is to say, one column has only one separation mode.), therefore, the number of columns is that n=2, q=0, m=2.

When a 2D column is used to achieve off-line and on-line 2D-LC on this multi-dimensional liquid chromatography separation system, $$n = q = 1 \quad (5)$$

$$m = 2 \quad (6)$$

5) Collect-reserve device. It includes "p" sample loops and sample loops switching units and "p" is greater than or equal to 2. The sample loops switching unit is used to control the liquid in the collect-reserve device to flow into at least one of the collect-reserve device selectively;

6) At least two draining devices. The liquid in the 2D-LC separation system is discharged out of the system through the draining devices.

7) Flow switching device. It is made up from valves connected with the device above and pipes. By switching the valves of the flow switching device, not only the flow path for conventional liquid chromatography separation but also the flow path for multi-dimensional liquid chromatography separation can be formed.

Wherein, in the first dimensional separation, the first infusion device will be applied to transfer mobile phase for the first dimensional separation to the first sample injection device (as shown in the 7 of FIG. 2, counted from left to right, the first one is a 2D chromatographic column and others are all conventional single-mode columns). The first injection device gets original samples from outside the system and pumps them into the separation device together with mobile phase from the first infusion device; samples from the first dimensional liquid chromatography separation and to be separated are separated by the separation device and different fractions are obtained; the intermediate fractions to be separated in the next dimension are stored in at least one of the sample loops of the collect-reserve device and fractions need not to be separated again are discharged out of the system from the draining device 2.

In the second dimensional separation, mobile phase suitable for liquid chromatographic separation are transported by the first infusion device to the collect-reserve device, and then, intermediate fractions stored in at least one of the sample loops flow together with the mobile phase into the injection mixer; mobile phase suitable for liquid chromatographic separation are transported by the second infusion device from the mobile phase tank to the injection mixer too. The injection mixer helps to mix the intermediate fractions and mobile phase from at least one of the sample loops with the mobile phase from the second infusion device and the second dimensional injection mixture with suitable composition is formed. And then, the second liquid chromatography separation is done for the injection mixture by the separation device and different fractions are obtained.

Wherein, the first and second infusion device adjust and measure the amount of mobile phase they transport for the second dimensional separation so that the eluent concentration of the injection mixture using in the second dimensional separation is lower than the critical migration eluent concentration on which all the protein in the intermediate fractions of the injection mixture must be retained in this second dimensional separation.

Preferably, the liquid chromatography separation system based on this invention can include the first, second and third liquid draining port. Wherein, the first draining device can discharge liquid waste from detection device outside the system, and the second draining device can discharge liquid waste from the original injected samples or the liquid storage device outside the system.

The third drainage device is specially designed for mass production. By connecting a two-port valve in parallel with the detector and adjusting the hole size of the two-port valve, 90% to 99.9% of the mobile phase containing the target products discharges out of the product collection device or waste collection device without getting through the detector and only 0.1% to 10% of the same mobile phase flow synchronously into the detector.

Preferably, the flow path switching device can constitute any kind of the following flow path selectively to switch flow path:

The conventional separation flow path, the mobile phase tank, first infusion device, first injector device, separation device, detection device and first and second drainage device are connected in turn in this flow path;

The first dimension separation flow path, the mobile phase tank, first infusion device, separation device, detection device, collect-reserve device and second drainage device are connected in turn in this flow path;

The second dimension separation flow path, the mobile phase tank, first infusion device, collect-reserve device, second injector device, separation device, detection device and first drainage device are connected in turn. What's more, the mobile phase tank, second infusion devices and second injection device are connected in turn in this flow path;

On the other hand, mD-LC separation method using for protein separation is provided in this patent and this mD-LC separation method includes the following steps:

1) pre-preparation: Make sure the critical migration eluent concentration under the condition of the second dimension or more multi-dimensional separation that all the target protein in the un-separated protein samples are retained;

2) the first dimensional separation: Separate the protein samples through the gradient elution on conventional liquid chromatography separation, thus different fractions are obtained;

3) collect and reserve the intermediate fraction: Collect and reserve the intermediate fraction of the fractions after the last dimensional separation, which need to be separated further;

4) the second dimensional or multidimensional separation: Mix all or part of the intermediate fraction to be separated in next dimension with mobile phase using in the next dimension together so that injection mixer is acquired. And then, the injection mixer is injected into the same mixed-mode chromatographic column or another mixed-mode chromatographic column in parallel with the first dimensional column using in the next dimensional separation. And then, through the gradient elution, as mentioned in step 4), the injection mixer retained in the chromatographic column using in the next dimensional separation is separated in the second dimension or more multi-dimensional liquid chromatography and once again, the different fractions are acquired. For all intermediate fraction that obtained from the last dimension and to be separated in the next dimension, such separation is done.

5) repeat the above steps 3) and 4), so as to get all of the target protein products.

Wherein, in the step 4), adjust and measure the amount of mobile phase for the next dimensional separation so that the eluent concentration of the injection mixture is lower than the critical migration eluent concentration on which all or part of the target protein in the target intermediate fractions must be retained in this second or more dimensional separation.

Preferably, in the mentioned step 4), the intermediate fractions are injected into the parallel chromatographic column through the high velocity mobile phase.

In this patent, the "high flow rate" mobile phase refers to that the flow rate of the mobile phase is higher than that of the mobile phase using in the liquid chromatography separation through the gradient elution.

More preferably, in the mentioned step 4), the injection time of said intermediate fractions of target protein to the chromatographic column should less than half of the time that intermediate fractions are separated.

The multi-dimensional liquid chromatography separation system based on this invention can be done both on-line and off-line.

In the "on-line fraction separation method", fractions after the previous dimension separation are collected on-line, and then, the intermediate fractions need to be separated again are send directly to the next dimensional separation.

In the "off-line fraction separation method", fractions after the previous dimension separation are collected off-line, and then, the intermediate fractions need to be separated again are send directly to the next dimensional separation.

The mD-LC separation method is carried out through the mD-LC separation system based on this invention.

The mD-LC separation method based on this invention can be carried out through the mD-LC separation system based on this invention. The steps are as follows:

1) pre-preparation: Make sure the critical migration eluent concentration $C_{CMP}$ under the condition of the second dimension or more multi-dimensional separation on which all the target proteins to be separated in the protein samples are retained;

2) the first dimensional separation: Through the flow switching device, the first dimensional separation flow path is formed; the mobile phase for the first dimensional separation is transported through the first infusion device and protein samples are injected into the mD-LC separation system through the first injector device. By switching the chromatography column switching unit, the column for the first dimensional separation is connected to the flow path; different fractions in the protein samples are separated by gradient elution, and detected by the detector.

3) collect and reserve the intermediate fraction: By switching the collection and reserve device switching unit, intermediate fractions to be separated again are collected and stored in different collect-reserve device and fractions need not to be separated again are discharged out of the system from the second draining device.

4) the second dimensional or multidimensional separation: After the last dimensional separation, by switching the flow path switching device, the flow path for the second or multi-dimensional separation is formed; by switching the chromatographic column selector valve, the column suitable for the second or multi-dimensional separation is connected to the flow path; mobile phase for the next dimensional separation is transported to the collect-reserve device through the first infusion device, so that the intermediate fractions to be separated in the next dimension flow from the corresponding collection and reserve device into the injection mixer of the second infusion device. At the same time, mobile phase for next dimensional separation is transported to the injection mixer through the second infusion device, so that the intermediate fractions mix with the mobile phase and the injection mixture is acquired; inject the injection mixture into the column for next dimensional separation, measure and adjust the mobile phase amount transported by the first and second infusion device, so that the eluent concentration of the injection mixture is lower than the critical migration eluent concentration on which all or part of the intermediate fractions must be retained in the next dimensional separation. In this way, the proteins are retained in the column and the second dimensional injection is completed.

And then, by gradient elution, the injection mixture is separated into different fractions in the column and detected by the detector;

All the intermediate fractions getting from the last dimension and to be separated in this dimension are all separated in this way in this step.

5) repeat the above steps 3) and 4), so as to get all of the target protein products.

6) the final dimension of multi-dimensional chromatography is desalination. Normally, SEC column is used.

Two-Dimensional Liquid Chromatography (2D-LC) Separation Method

Specially, a 2D-LC separation method with a single column using for protein separation is provided in this patent and this 2D-LC separation method includes the following steps:

1) Pre-preparation: Make sure the critical migration eluent concentration under the condition of the second dimension separation that all the target protein in the un-separated protein samples are retained;

2) The first dimensional separation: Separate the protein samples through the first dimensional separation using a conventional single-mode column, as shown in FIG. 2, thus different fractions are obtained;

3) Collect and reserve the intermediate fraction: Collect and store the intermediate fraction of the fractions after the first dimensional separation, which need to be separated in the second dimensional separation;

4) The second dimensional separation: Mix the intermediate fraction with mobile phase using in the second dimension together so that injection mixer is acquired. And then, the injection mixer is all or partly injected into the chromatographic column for the second dimensional separation; and then, the injection mixer retained is separated in the second dimension and target protein product is acquired. For all intermediate fraction that obtained from the first dimension and to be separated in the second dimension, such separation is done.

Wherein, in the step (4), adjusting and measuring the mobile phase for the second or more dimensional separation so that the eluent concentration of the injection mixture is lower than the critical migration eluent concentration on which all the proteins in the intermediate fractions must be retained in the second dimensional separation.

The 2D-LC separation method is carried out through the multi-dimensional separation system or 2D-LC separation system based on this invention.

The 2D-LC separation method or the multi-dimensional separation system based on this invention can be carried out through the 2D-LC separation system based on this invention. The steps are as follows:

1) Pre-preparation: Make sure the critical migration eluent concentration $C_{CMP}$ under the condition of the second dimension separation on which all the proteins to be separated in the protein samples are retained;

2) The first dimensional separation: Through the flow switching device, the first dimensional separation flow path is formed; mobile phase for the first dimensional separation is transported through the first infusion device and pass through the first sample injection device. As shown in FIG. 2, a conventional single-mode column is used. Inject the protein samples into the mD-LC separation system; by switching the chromatographic column selector valve, the column for the first dimensional separation is connected to the flow path; different fractions in the protein samples are separated by gradient elution, and detected by the detector.

3) Collect and store the intermediate fraction: By switching the collect-reserve device switching unit, intermediate fractions to be separated again are collected and stored in different collect-reserves and fractions need not to be separated again are discharged out of the system from the second draining device.

4) The second dimensional separation: After the previously dimensional separation, by switching the flow path switching device, the flow path for the second separation is formed; by switching the chromatographic column selector valve 6-1, the single-mode column for the second dimensional separation is connected to the flow path to do the second dimensional separation; mobile phase for the second dimensional separation is transported to the collect-reserve device through the first infusion device, so that the intermediate fractions to be separated in the second dimension flow from the corresponding collect-reserve device into the injection mixer of the second infusion device. At the same time, mobile phase for second dimensional separation is transported to the injection mixer through the second infusion device, so that the intermediate fractions mix with the mobile phase and the injection mixture is acquired; inject the injection mixture into the column for second dimensional separation, measure and adjust the mobile phase amount transported by the first and second infusion device, so that the eluent concentration of the injection mixture is lower than the critical migration eluent concentration on which all the intermediate fractions must be retained in the second dimensional separation. In this way, the proteins are retained in the column and the second dimensional injection is completed; by gradient elution, the injection mixture is separated into different fractions in the column and detected by the detector through the chromatographic column selector 6-2; all the intermediate fractions getting from the first dimension and to be separated in the second dimension are all separated in this way in this step.

Buffer Exchange and Chromatographic System Re-Equilibrium

Before or after the sample injection in said step (4), when the mobile phase composition of the intermediate fractions after the previously dimensional separation does not match the mobile phase composition of the next dimensional separation, the mD-LC separation method or two-dimensional liquid chromatography separation method based on this invention can also include the steps as follows:

Buffer exchange: mobile phase using in the next dimensional separation is used as buffer and the buffer flow through the next dimension separation column. Wherein, the buffer elution concentration is lower than the critical migration eluent concentration on which all the proteins of the intermediate fractions to be separated in the next dimensional separation can retain, so that at least part of the original mobile phase in the column is replaced.

For example, collection liquid containing the target protein from the previously dimensional separation is the mixture of solution 1 and solution 2 with known composition. The mixture composition can be estimated according to gradient time and the composition of solution 1 and solution 2. However, different proteins have different retention time, so the composition of different protein collection liquid is not fixed and we can use solution X to represent. The collection liquid is normally more than 3 mL and when this collection liquid is pumped into the second injection device by solution 1 and solution 2, it will not mix with the driving fluid. Therefore, after mix the solution 3 or 4 driven by the second infusion device with solution X in the second injection device, the whole process that from the start to the solution is quantitatively into the second dimension chromatographic separation column is called sample-buffer exchange or simply buffer exchange.

Chromatographic system re-equilibrium: During the process of solution X injecting, the mobile phase left in the column for the first dimensional separation is replace partly, which helps the re-equilibrium of the chromatography system. It can be regarded partly as the second dimensional chromatography system re-equilibrium process. To continue accomplishing the complete equilibrium, just use solution 3 or 4 to pass through the chromatographic column.

After buffer exchange and chromatographic system re-equilibrium is carried out, the intermediate fractions separation is done.

Preferably, the flow rate of the buffer exchange and chromatography system re-equilibrium is higher than that of the gradient elution used in the liquid chromatography separation.

Preferably, buffer exchange can be implemented through the present mD-LC separation system. Wherein, mobile phase using in the next dimensional separation is used as buffer and through the first infusion device or second infusion device, the mobile phase flows through the column for next dimensional separation. Wherein, the buffer concentration is lower than the critical migration eluent concentration on which all the proteins of the intermediate fractions to be separated in the next dimensional separation can retain, so that at least part of the original mobile phase in the column is replaced. Preferably, the flow rate of the buffer transported by the first and/or second infusion device is higher than that of the gradient elution used in the liquid chromatography separation.

In particular, before or after the sample injection the step (4), the 2D-LC separation method based on this invention can include steps as follows:

Buffer exchange: mobile phase using in the second dimensional separation is used as buffer and the buffer flow through the second dimension separation column. Wherein, the buffer elution concentration is lower than the critical migration eluent concentration on which all the proteins of the intermediate fractions to be separated in the second dimensional separation can retain, so that at least part of the original mobile phase in the column is replaced. Preferably, the flow rate of the buffer transported by the first and/or second infusion device is higher than that of the gradient elution used in the liquid chromatography separation.

After buffer exchange and chromatographic system re-equilibrium is accomplished, the second dimension separation for intermediate fractions is done.

Column Regeneration

Chromatographic columns need to be re-generated periodically. The columns can be cleaned with suitable strong elution solution in high flow rate. Technicians in this field can chose the suitable strong elution solution through the chromatographic separation mode used.

By reading the disclosed technical content of this patent, technicians in this field can understand easily that the inventors discover the protein "steady-migratory" phenomenon and apply it creatively in the liquid chromatography separation technology and design the mD-LC separation system and mD-LC separation method of this invention. Wherein, by controlling the eluent concentrations of the sample mixture re-injected is lower than the critical migration eluent concentration on which all the proteins to be separated in the next dimensional separation can retain, all the fractions from the previous dimensional separation are injected into the next dimensional separation column without desalting or any special interface.

Advantages of the invention lie in particularly that the quantitative transfer of all the target intermediate fractions can be achieved, so as to realize the fast separation of proteins and peptides.

Figure 2:
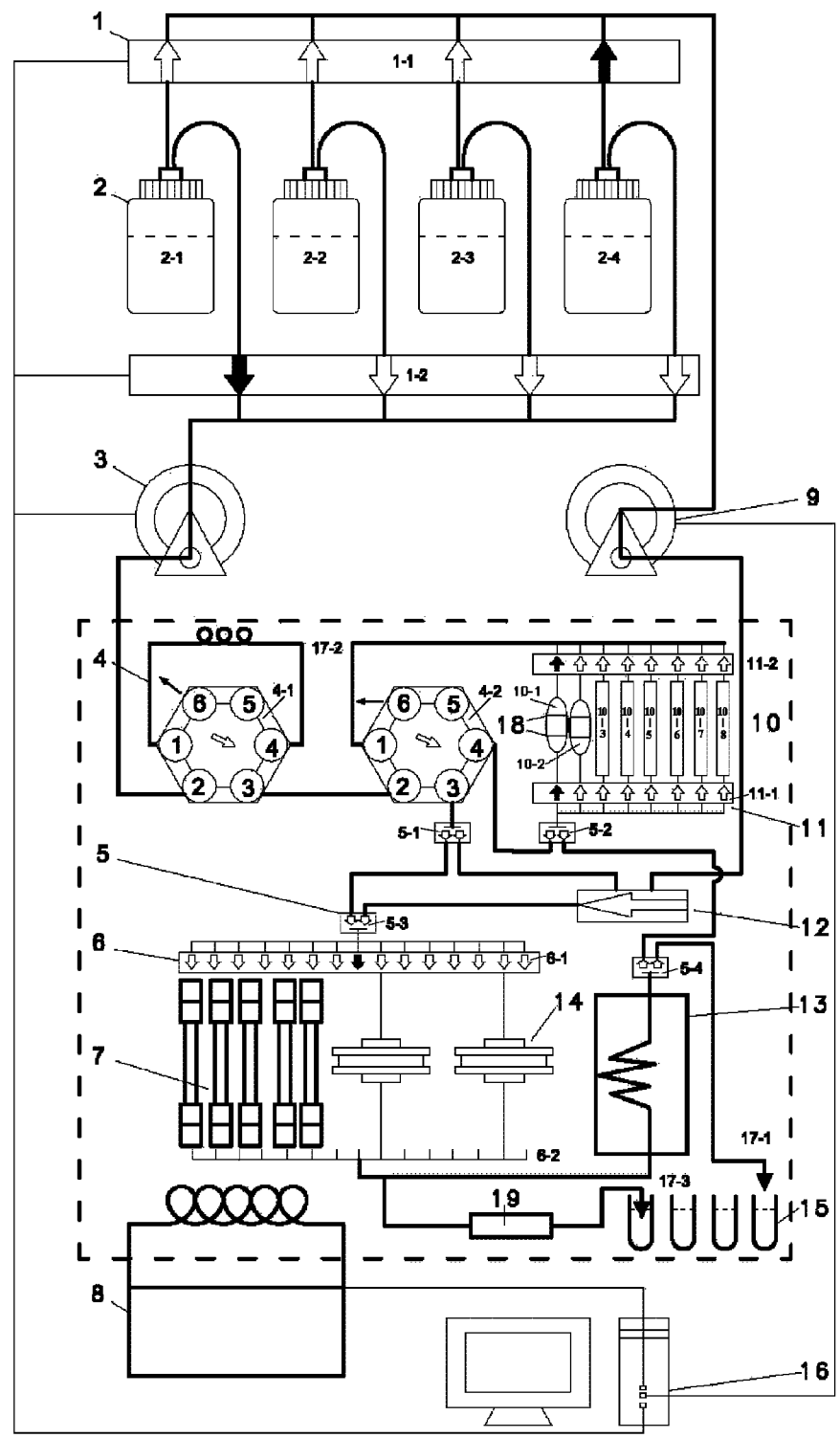
FIG. 2 shows the flow path structure of the mD-LC separation system example.

The components of the FIG. 2 are: 1. four channel gradient unit; 2. mobile phase tank; 2-1. solution 1; 2-2. solution 2; 2-3. solution 3; 2-4. solution 4; 3. pump A; 4. six-port valve groups: Including one six-port injection valve and one conventional six-port valve; 4-1. six-port injection valve, 4-1 is the first sample (original sample) injection device; 4-2. six-port valve 4-2: This six-port valve 4-2 is connected with related valves and mixer 12 to form the second sample injection device; 5-1 to 5-4. four three-port valves; 6. multi-port valve groups: Including two multi-port valves; 6-1. multi-port valve; 6-2. Fluid flow into the chromatographic column or cake groups 7 through multi-port valve; 7. chromatographic column or cake groups; 8. constant low temperature control tank device (including Sterilization Device); 9. pump B; 10-1 to 10-8. collect-reserve device; 11. multi-port valve groups: Including two eight-port valves; 11-1. eight-port valves 1; 11-2. eight-port valves 2; 12. mixer; 13. detector; 14. chromatographic cake; 15. fraction collector; 16. work station; 17. draining port: Including two draining ports; 17-1. main draining port; 17-2. the waste draining port for two-dimensional injection; 17-3.

the draining port for purifying protein in large scale; 18. oscillator; 19. parallel shunting tubes. As shown in the FIG. 2, thick solid line refers to pipeline and thin solid line refers to data line.

Figure 3:
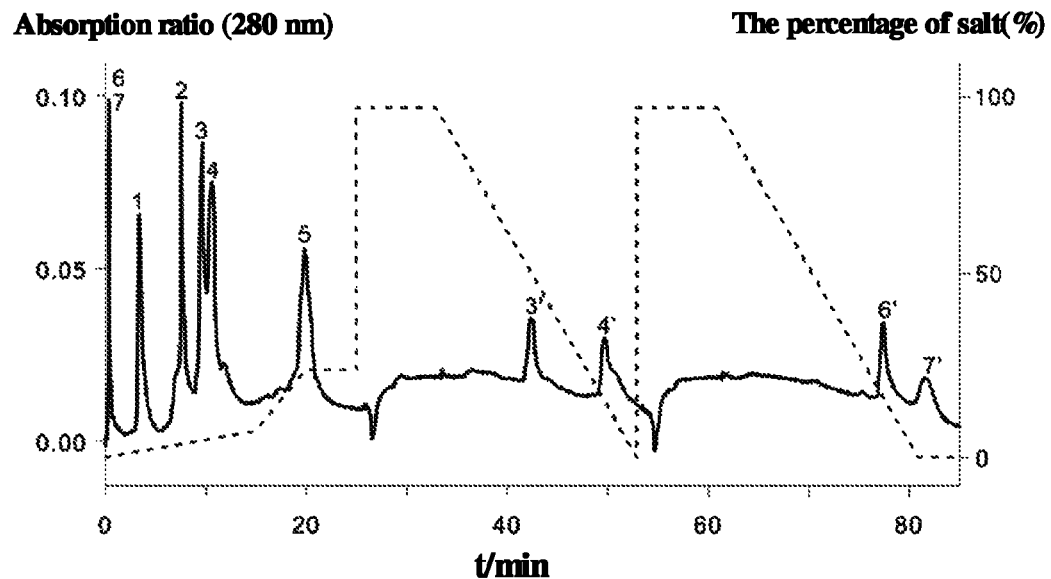

FIG. 3 shows the 2D-LC (WCX, HIC) separation result of 7 proteins by Aolan commercial WCX column.

Figure 4:
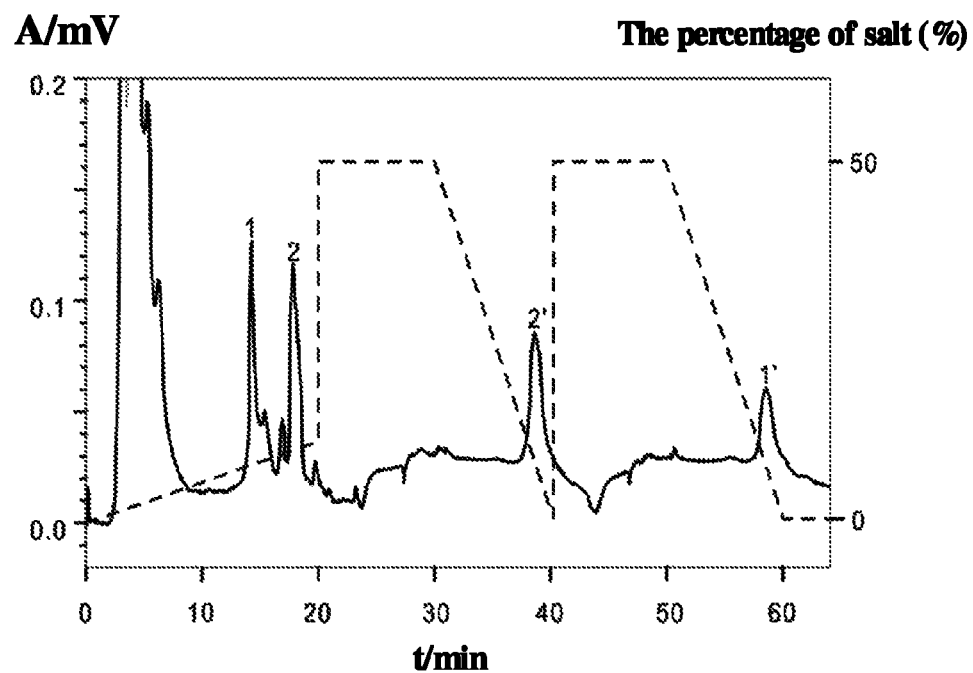

FIG. 4 shows the purification and desalination result of protein α-chymotrypsin and trypsin under the condition of 3D-LC (WCX/HIC/SEC) with the commercial Shim-pack PA-CM WCX column and TSKgel G4000 SW XL SEC desalting column.

Figure 5:
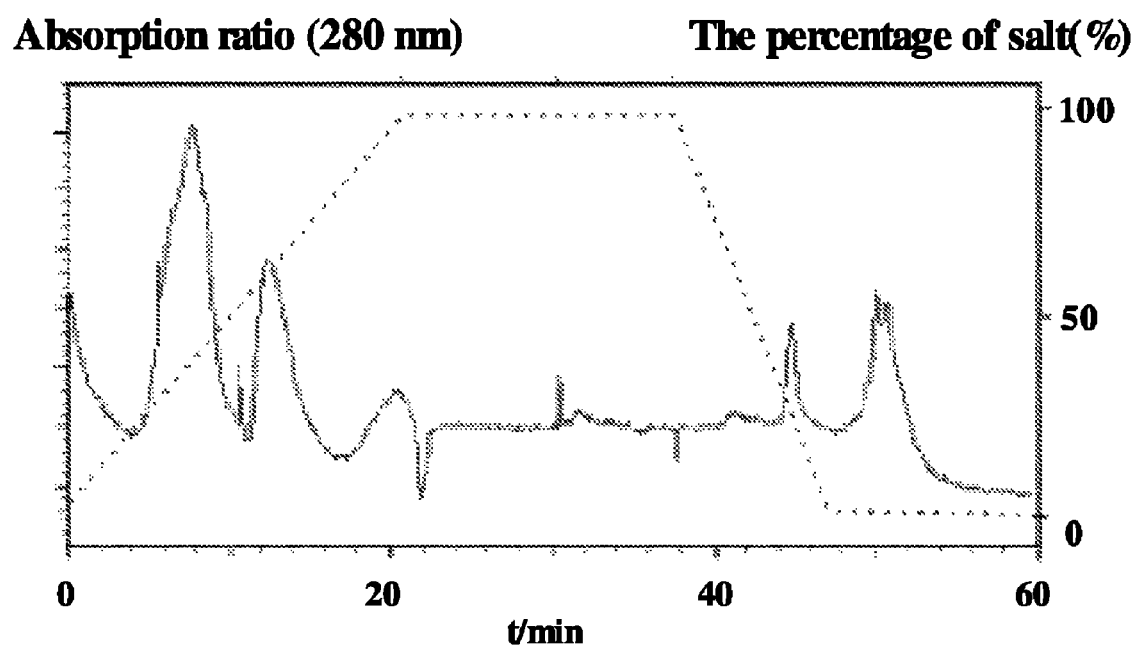

FIG. 5 shows the result of rapid purification of bovine pancreas cytochrome C by on-line single-column two-dimensional liquid chromatography column [2D (WCX, HIC) column].

DETAILED DESCRIPTION OF THE EMBODIMENTS

Technical solution of the invention is illustrated with detailed embodiments hereinbelow, the embodiments, however, should not be explained as limitation of the protection range of the invention.

The technical points and advantages of this present invention will be obvious by reading the following specific implements.

Two-dimensional Liquid Chromatography (2D-LC) Separation System

In particular, in a particular implement as shown in FIG. 2, it is the 2D-LC separation system of mD-LC with hydrophobic interaction chromatography (HIC) and ion exchange chromatography (IEC), which includes:

(a) Four storage tanks act as mobile phase reservoir (mobile phase tanks 2-1 to 2-4), its volume and materials can vary with the system scale, from 100 mL to 100 L, from glass to stainless material etc. Wherein, the mobile phase tanks 2-1 to 2-4 have solutions for liquid chromatography in reserve respectively. The solutions are marked solution 1-2 and they are respectively the HIC mobile phases A and B. Solution 3-4 is respectively the IEC mobile phases A and B. Wherein, solutions 1 and 2 are used as the first dimensional chromatography separation mobile phase and solutions 3 and 4 are used as the second dimensional chromatography separation mobile phase.

(b) Pump A (3) and four channel gradient units 1-2 act as the first infusion device and pump B (9) and four channel gradient unit 1-1 act as the second infusion device. The four channels are connected to the mobile phase tanks 2-1 to 2-4 in correspondence and they can adjust and measure the flow rate independently.

Wherein, pump A (3) and four channel gradient unit 1-2, pump B (9) and four channel gradient unit 1-1 can be commercial four channel gradient pump and the flow rate of different channels can be transported and measured depend on the pump power themselves.

Pump A (3) and four channel gradient unit 1-2 are used mainly for the first dimensional chromatography separation. They also can be used for transfer the first dimensional fraction reserved in the collect-reserve device for the second dimensional injection or separation. Pump B (9) and four channel gradient unit 1-1 are always combined with pump A (3) and used mainly for the second or multi-dimensional injection and separation.

Pump A (3) and pump B (9) are both high pressure pumps. The flow rate is preferably from 0.001 to 10 mL/min; precision is ±0.001 mL; the highest pressure is 40 MPa. For preparative multidimensional liquid chromatography separation system, the flow rate of pump A (3) and pump B (9) is preferably from 0.01 to 100 mL/min; precision is ±0.01 mL; the highest pressure is 20 MPa; for productive multidimensional liquid chromatography separation system, the flow rate of pump A (3) and pump B (9) is preferably from 0.1 to 10 L/min; precision is ±0.1 mL; the highest pressure is 20 MPa.

(c) The six-port valve 4-1 acts as the first injection device and the six-port valve 4-2 acts as the second injection device.

Wherein, six-port valve 4-1 is used as first dimensional injection valve and first draining valve; six-port valve 4-2 is the second dimensional injection valve. The valve is marked obviously "inject" and "load" two positions to represent the two dimensional chromatography separation system working situation.

The six-port valve 4-1 has six ports. Port 1 and port 4 are connected with sample loop and port 6 is connected with the injector draining port. The sample volume is for example, 10 mL. The internal structure of the six-port valve 4-1 is: In injection state, port 1 and port 2 of the six-port valve 4-1 are connected, port 3 and port 4 are connected, port 5 and port 6 are connected; in the non-injection or pre-injection state, port 1 and port 6 are connected, port 2 and port 3 are connected, port 4 and port 5 are connected. Port 1 and port 2 of the six-port valve 4-1 are connected respectively with the two ends of the sample loop; port 6 is connected with the injector draining port.

The mixer 12 is for example, nozzle pipeline mixer which has two mixer inlets (mixer inlet M1 and mixer inlet M2) and one mixer outlet M0. The inlet M1 of the mixer 12 is connected with the outlet of pump B (9). Mixer 12 helps to mix the previous dimensional fractions with the mobile phase for next dimensional separation at an appropriate ratio, so that the mixture concentration is lower than the "lowest eluent concentration" for the two-dimensional chromatographic separation request. The six-port valve 4-2 and the mixer form together the second injection device.

(d) The separation device is made of chromatographic column group 7 or chromatographic cake group 14, chromatographic column switching unit, namely the multi-way valves 6-1 and 6-2 and the pipelines connecting those parts. Multi-port valves 6-1 and 6-2 are used to control the target protein flow into one column or cake with required separation mode of the chromatographic column group 7 or chromatographic cake group 14.

The chromatographic column group 7 or chromatographic cake group 14 includes a lot of commercial chromatographic columns, mixed-mode chromatographic columns, or commercial chromatographic cakes which is well known by technicians in the field and mixed-mode chromatographic cakes normally used for protein separation and the total number is n. For brevity, these chromatographic columns or cakes are denoted for chromatographic column 1, column 2, column, 3 etc., and chromatographic column n. Multi-port valves 6-1 have one inlet and at least n outlet (denoted respectively for outlet 1, outlet 2, outlet 3, etc. and outlet n). Multi-port valves 6-2 have one outlet and n inlet (denoted respectively for inlet 1, inlet 2, inlet 3, etc. and inlet n). The inlet 0 of the multi-port valves 6-1 are the inlet of the separation device and the outlet 0 of the multi-port valve 6-2 is the outlet of the separation device. The outlet 1-$n$ of the multi-port valve 6-1 are connected respectively one by one with the inlet of chromatographic column 1-$n$ and the inlet 1-$n$ of the multi-port valve 6-2 are connected respectively one by one with the outlet of chromatographic column 1-$n$. The internal structure of the multi-port valves 6-1 and 6-2 are that when switching to one chromatographic column α (a stands for natural number from 1 to n.), the inlet 0 of the multi-port valve 6-1 is connected with the outlet α corresponding to the chromatographic column α and the outlet 0 of the multi-port valve 6-2 is connected with the inlet α corresponding to the chromatographic column α.

Wherein, the chromatographic cake group 14 can be set to variety of chromatographic separation medium loading in stainless or polymeric material cake-shape cavity. It can be one-dimensional, two-dimensional or even multi-dimensional modes and installed in parallel together with other chromatographic columns as member of the chromatographic column group 7. Through the multi-port valves 6-1 and 6-2, chromatographic cake group 14 are connected with the chromatographic system to implement various kinds of multi-dimensional chromatography separation.

(e) The detector device is detector 13, which is the detector for conventional protein detection well-known by technician personal in this field. UV detector, different refractive index detector, electrochemical detector and mass spectrum can all be used. All detector for detecting proteins and peptides can be used and all these detectors can be commercially obtained.

(f) The collect-reserve device is made of eight liquid tubes (denoted for liquid storage tubing 10-1 to 10-8) which is regarded as collect-reserve equipment, the eight-port valves 11-1 and 11-2 which act as collect-reserve equipment switching valve, and the pipelines connecting those parts.

The collect-reserve is consisted of materials of stainless steel, peek tube or titanium steel. It can be spiral tubular shapes, olive-shaped hollow tube with different capacity and shapes to and reserves to accommodate and store effluent. One side of the collect-reserve device is connected with eight-port valve 11-1, another side with eight-port valve 11-2.

The eight-port valve 11-1 and 11-2 are connected respectively to the two ends of the 8 liquid collect-reserve devices. Each channel is connected with one liquid collect-reserve device, so that fractions are controlled to flow into the corresponding liquid collect-reserve devices.

Wherein, the liquid collect-reserve devices 10-1 to 10-8 have the same volume of at least 2 mL or they have different volumes ranging from 2 mL to 2 L. Eight-port valve 11-1 has one inlet and 8 outlet (outlet 1 to 8), and eight-port valve 11-2 has one outlet and 8 inlet (inlet 1 to 8). The inlet 0 of the eight-port valve 11-1 acts as the inlet of the liquid collect-reserve device and the outlet 0 of the eight-port valve 11-2 acts as the outlet 0 of the liquid collect-reserve device. The outlet 1-8 of 11-1 are connected respectively one by one with the one end of the liquid collect-reserve device 10-1 to 10-8 and the inlet 1-8 of the eight-port valve 11-2 are connected respectively one by one with the other end of the liquid collect-reserve device 10-1 to 10-8. The internal structure of the eight-port valve 11-1 and 11-2 are that when switching to the 10-β position (β stands for natural number from 1 to n.) of the liquid collect-reserve device, the inlet 0 of the eight-port valve 11-1 is connected with the outlet β and the outlet 0 of the eight-port valve 11-2 is connected with the inlet β. Under the condition of switching to one of the liquid reserve tubes, liquid can pass through the eight-port valve 11-1, the liquid collect-reserve device and eight-port valve 11-1 in turn; at the same time, the eight-port valve 11-1 and 11-2 both allow the liquid flow in reverse direction through the valve. At that time, liquid can pass through the eight-port valve 11-2, the liquid collect-reserve device and eight-port valve 11-2 in turn.

Oscillator 18 is used to stir the collection liquid stored in the olive-shaped liquid collect-reserve device so that the collection liquid is well mixed. And then, the protein solution is desalinated. Or the oscillator 18 is used when part of the collection liquid is injected for next dimensional separation.

(g) Acting as the first draining device, the draining port 17-1 is connected with port 2 of the three-port valve 5-4; acting as the second draining device, the draining port 17-2 is connected with port 6 of the six-port valve 4-2.

There are three draining ports: the main draining port 17-1 connecting with the fraction collector, draining port 17-2 as waste draining port of second dimensional injection and draining port 17-3 for protein large-scale purification.

Draining port 17-3 includes the parallel shunt 19 in parallel with the detector 13. In large-scale purification of proteins, to prevent from the high pressure generated by the detection cell when high flow rate liquid pass through the detector, more than 90% of the mobile phase pass through the parallel shunt and flow into the fraction collector 15 and only 1% to 10% of the mobile phase flow into the detection cell to achieve protein "on-line detection".

Fraction collector 15 is used specially for the collection of final product after purification. Of course, it also can be used to collect intermediate fractions. Fraction collector 15 can be commercially obtained.

(h) The six-port valve 4-2, three-port valve 5-1, three-port valve 5-2, three-port valve 5-3, three-port valve 5-4 and pipelines connecting those valves act together as the flow path switching device.

Wherein, six-port valve 4-2 has 6 ports (port 1 to port 6), three-port valves 5-1, 5-2, 5-3, and 5-4 each has three ports (port 1, port 2 and port 3). The internal structure of the six-port valve 4-2 is that, when this six-port valve 4-2 is in the first switch position 4-2a, port 1 and port 2 are connected, port 3 and port 4 are connected and port 5 and port 6 are connected; when this six-port valve 4-2 is in the second switch position 4-2b, port 1 and port 6 are connected, port 2 and port 3 are connected and port 4 and port 5 are connected. The internal structure of the three-port valve 5-1, 5-2, 5-3, and 5-4 are that, when this three-port valve 5-1, 5-2, 5-3, and 5-4 are in the first switch position 5-1a, 5-2a, 5-3a and 5-4a, for each valve, port 1 and port 2 are connected; when this three-port valve 5-1, 5-2, 5-3, and 5-4 are in the second switch position 5-1b,5-2b,5-3b and 5-4b, for each valve, port 1 and port 3 are connected. Port 2 of the six-port valve is connected with the pump 1 outlet. Detector inlet is connected with the inlet 0 of the multi-port valve 6-2 which acts as the separation device; detector outlet is connected with port 3 the three-port valve 5-4. Port 1 of the six-port valve 4-2 is connected with outlet 0 of the eight-port valve 11-2; port 2 of the six-port valve 4-2 is connected with port 3 of the six-port valve 4-1; port 3 of the six-port valve 4-2 is connected with port 1 of the three-port valve 5-1; port 4 of the six-port valve 4-2 is connected with port 2 of the three-port valve 5-2; port 6 of the six-port valve 4-2 is connected with draining port 17-2. Port 2 of the three-port valve 5-1 is connected with mixer inlet M2; port 3 of the three-port valve 5-1 is connected with port 2 of the three-port valve 5-3; port 1 of the three-port valve 5-2 is connected with inlet 0 of the multi-port valve 1, which acts as the separation device inlet; port 3 of the three-port valve 5-3 is connected with mixer outlet M0; port 1 of the three-port valve 5-3 is connected with inlet 0 of the multi-port valve 1; port 3 of the three-port valve 5-2 is connected with port 3 of the three-port valve 5-4; port 2 of the three-port valve 5-4 is connected with draining port 17-1.

(i) The constant low temperature controlling tank 8 acting as the constant temperature device, this constant low temperature controlling tank keeps all the components, as shown in the dotted box in the picture, on the constant temperature 4° C.

This constant low temperature controlling tank includes the sterilization device, which is a constant temperature tank equipped with a cooling means, so that the space inside can stay at a constant temperature 4° C. At the same time, the collect-reserve device or the entire multi-dimensional liquid chromatographic separation system are accommodated in this space. The constant temperature device can be assembled all or partly with other parts of the chromatograph into a shell and to be a whole systems. It also can be installed separately as an independent system.

The sterilization device includes steam generator device and steam injection device or electric heating device. The steam generator device can produce steam with a temperature of more than 140° C. and the steam injection device pushes the steam into the collect-reserve device of the multi-dimensional liquid chromatography separation system.

The sterilization device includes electric heating device which is heated through the electric power directly, or the hot air generating from the electric heating.

(j) The computer control device acting as the automatic control device. This computer control device can to automatically control the operation of the four channel gradient unit 1-1 and 1-2, pump A (3) and pump B (9) and constant low temperature controlling tank 8, and at the same time, receive signals from the detector 13.

Special operating software is designed for work station 16 based on the system type: independent type or integral type. The former is usually used together with conventional liquid chromatograph, therefore the system is only used with chromatographic system and its software is just a kind of design;

While the latter considers both the conventional chromatograph software and the multi-dimensional chromatography system designed in the patent, as whole design software, eventually become a workstation without containing any conventional chromatography workstation.

By switching the six-port valve 4-2, three-port valve 5-1, three-port valve 5-2, three-port valve 5-3 and three-port valve 5-4 of the flow path switching device, different kinds of flow paths are formed.

(A) Conventional separation flow path: six-port valve 4-2 is switched to position 4-2*b* (Port 1 and port 6 are connected, port 2 and port 3 are connected and port 4 and port 5 are connected.); three-port valve 5-1 is switched to position 5-1*b* (Port 1 and port 3 are connected.); three-port valve 5-2 can be any position; three-port valve 5-3 is switched to position 5-3*a* (Port 1 and port 2 are connected.); three-port valve 5-4 is switched to position 5-4*a* (Port 1 and port 2 are connected.). Thus, the conventional separation flow path, which connect the mobile phase tank, four channel gradient unit 1-2, pump A (3), chromatographic column group 7 or chromatographic cake group 14, detector 13 and the draining port 17-1 in turn, is formed.

On one hand, in the conventional separation flow path valve state above, the six-port valve 4-1 is further switched to injection state (Port 1 and port 2 are connected, port 3 and port 4 are connected and port 5 and port 6 are connected.), so that the sample loop is connected to the two dimensional liquid chromatography separation system flow path based on the present invention. Thus the injection state of the conventional separation flow path (called flow path A0) is formed.

On the other hand, in the conventional separation flow path valve state above, six-port valve 4-1 is further switched to non-injection state (Port 1 and port 6 are connected, port 2 and port 3 are connected and port 4 and port 5 are connected.), so that the sample loop is not connected to the two dimensional liquid chromatography separation system flow path based on the present invention. Thus the non-injection state of the conventional separation flow path (called flow path A) is formed.

(B) The first dimensional separation flow path: six-port valve 4-2 is switched to position 4-2*b* (Port 1 and port 6 are connected, port 2 and port 3 are connected and port 4 and port 5 are connected.); three-port valve 5-1 is switched to position 5-1*b* (Port 1 and port 3 are connected.); three-port valve 5-2 is switched to position 5-2*b* (Port 1 and port 3 are connected.); three-port valve 5-3 is switched to position 5-3*a* (Port 1 and port 2 are connected.); three-port valve 5-4 is switched to position 5-4*b* (Port 1 and port 3 are connected.). Thus, the first dimensional separation flow path, which connect the mobile phase tank, four channel gradient unit 1-2, pump A (3), chromatographic column group 7 or chromatographic cake group 14, detector 13, liquid reserve tubing group 10 and the draining port 17-2 in turn, is formed.

On one hand, in the flow path valve state mentioned above, the six-port valve 4-1 is further switched to injection state (Port 1 and port 2 are connected, port 3 and port 4 are connected and port 5 and port 6 are connected.), so that the sample loop is connected to the two dimensional liquid chromatography separation system flow path based on the present invention. Thus the injection state of the first dimensional separation flow path (called flow path B0) is formed.

On the other hand, in the flow path valve state mentioned above, six-port valve 4-1 is further switched to non-injection state (Port 1 and port 6 are connected, port 2 and port 3 are connected and port 4 and port 5 are connected.), so that the sample loop isn't connected to the two dimensional liquid chromatography separation system flow path based on the present invention. Thus the first dimensional separation flow path of the multi-dimensional liquid chromatography system based on this invention (called flow path B) is formed.

(C) The second dimensional separation flow path: six-port valve 4-2 is switched to position 4-2*a* (Port 1 and port 2 are connected, port 3 and port 4 are connected and port 5 and port 6 are connected.); three-port valve 5-1 is switched to position 5-1*a* (Port 1 and port 2 are connected.); three-port valve 5-2 is switched to position 5-2*a* (Port 1 and port 2 are connected.); three-port valve 5-3 is switched to position 5-3*b* (Port 1 and port 3 are connected.); three-port valve 5-4 is switched to position 5-4*a* (Port 1 and port 2 are connected.). Thus, the second dimensional injection and separation flow path, which connect the mobile phase tank, four channel gradient unit 1-1, pump A (3), liquid reserve tubing group 10 and the draining port 17-1 in turn and connected four channel gradient unit 1-1, pump B (9) and mixer 12 in turn, is formed.

Generally speaking, in the second dimensional separation flow path valve state of the two dimensional liquid chromatography separation system based on this invention, the six-port valve 4-2 is switched to non-injection state (Port 1 and port 6 are connected, port 2 and port 3 are connected and port 4 and port 5 are connected.). Thus the second dimensional separation flow path without intermediate fractions collection (called flow path C) is formed.

Conventional Liquid Chromatography Separation (One Dimensional Liquid Chromatography Separation)

Following the steps shown in FIG. 2 and operating the 2D-LC separation system based on this invention, the conventional liquid chromatography separation (one dimensional liquid chromatography separation) for protein samples can be realized:

(1) According to the knowledge which is well-known by technicians in this field, select mobile phase with suitable composition, turn on the pump A (3), set the suitable gradient elution conditions, including the initial concentration, linear or non-linear gradient elution, gradient time etc. Through the four channel gradient unit 1-2, suitable solvent is removed and transported from the mobile phase tank in a suitable flow rate (For example, solvent 1 and solvent 2 are removed and transported respectively from mobile phase tank 1 and mobile phase tank 2.). And, the separation device is connected to any chromatographic columns or cakes, so that necessary equilibrium is done for the chromatographic system.

(2) Sample Injection: six-port valve 4-1 is switched to non-injection state (Normally marked "load" on the valve. Here, port 1 and port 6 are connected, port 2 and port 3 are connected and port 4 and port 5 are connected.). Inject some protein sample mixture through port 5 of the six-port valve 4-1 (For example, 100 µL.) and hold the sample in the sample loop. Then, turn the injection valve to the position marked "inject", samples are injected into the chromatography separation device.

The injection valve is set to form the flow path A0 (the conventional separation flow path for injection) now. Meanwhile, the control system of the mD-LC system will command the gradient elution system to work synchronously. In this way, sample injection is completed.

(3) Conventional liquid chromatography separation: After sample injection, as shown in FIG. 2, the 2D-LC separation system based on this invention will back to the state flow path A (the conventional separation flow path for non-injection).

Through gradient elution, protein samples are separated into different fractions due to different retention time in the chromatographic column or cake and the fractions are detected in detector 13. Separated sample is discharged out of the system and collected from the draining port 17-1.

In a specific implement, the gradient elution in above step (1) is linear gradient elution.

In a specific implement, the gradient elution in above step (1) is non-linear gradient elution.

In a specific implement, the gradient elution in above step (1) is linear gradient elution under the condition of asynchronous injection.

According to properties of proteins to be separated, it is easy for technicians in this field to select the suitable chromatographic column and mobile phase for liquid chromatographic separation. In the way well-known in this field, it is easy for technicians in this field to determine the solvent flow rate of pump A (3).

2D-LC Separation Process

Now, we use the liquid chromatography separation system shown in FIG. 2 as an example to describe the operation process of the 2D-LC separation of liquid chromatographic separation system based on this invention.

Calculation of the critical migration time $t_{CMP}$ and critical migration eluent concentration $C_{CMP}$ Now we use FIG. 1 as an example to illustrate how to calculate method $t_{CMP}$ and $C_{CMP}$. FIGS. 1A, 1B and 1C, are respectively the gradient elution separation chromatograms (The liquid chromatography separation method is conventional liquid chromatography separation.) of benzyl alcohol (which is a small organic molecule.), carbonic anhydrase (protein, macromolecules) and the 15-peptide (GEPPPGK-PADDAGLV) (SEQ ID NO: 1) under the condition of asynchronous injection (namely injection time is different from gradient time. In FIG. 1, the latter injection time is one minute later than the former one.).

Figure 1A:
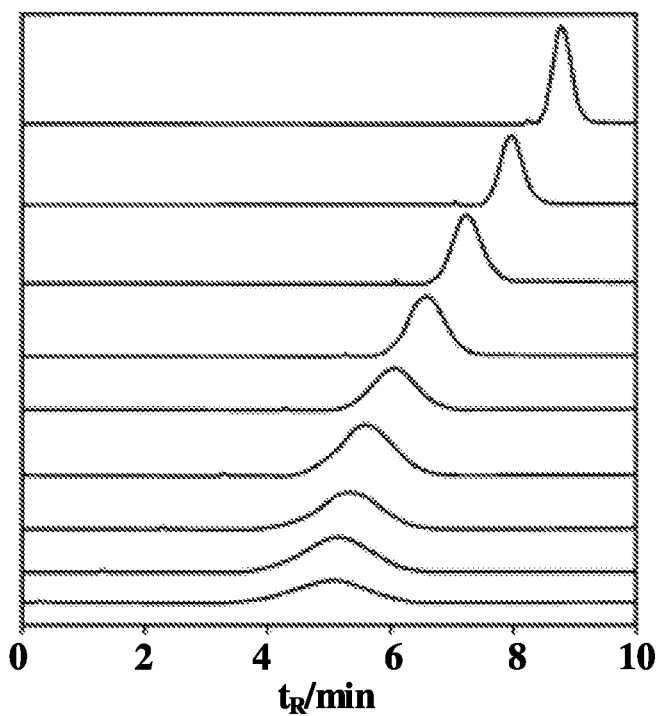
FIGS. 1A-1F show the result of RPLC linear gradient elution of benzyl alcohol, carbonic anhydrase, fifteen peptides (GEPPPGKPADDAGLV) (SEQ ID NO: 1) under the condition of asynchronous injection.
Figure 1B:
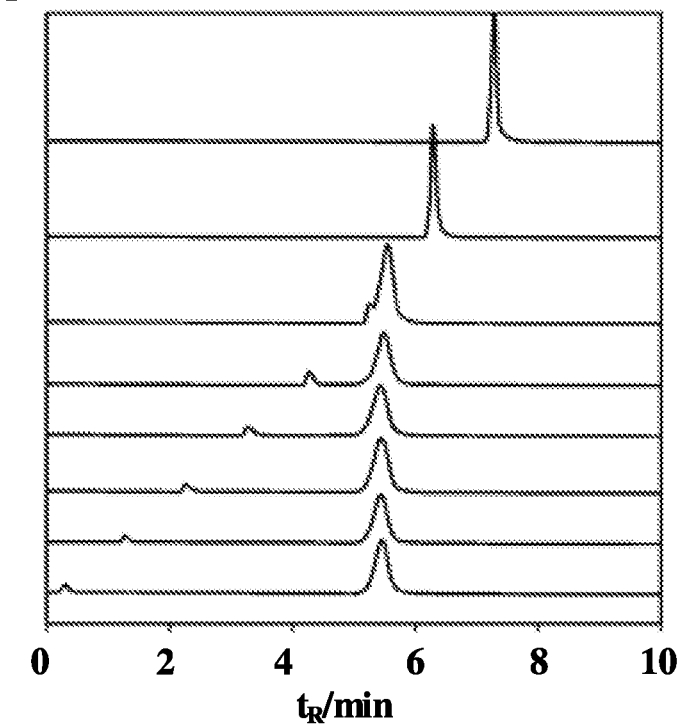
Figure 1C:
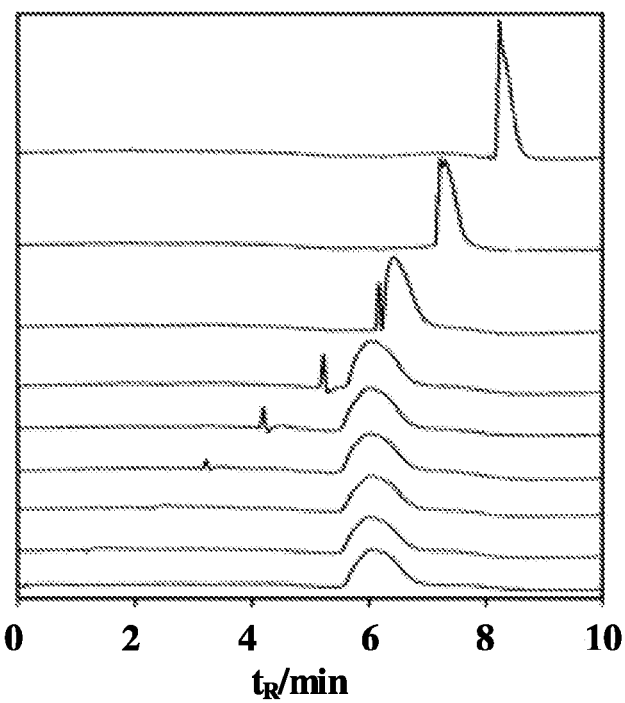
Figure 1D:
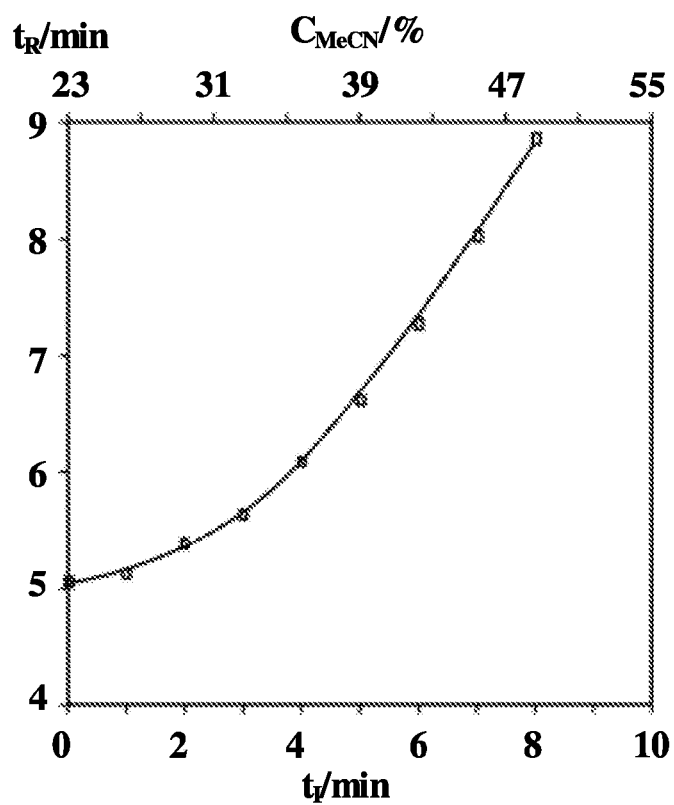
Figure 1E:
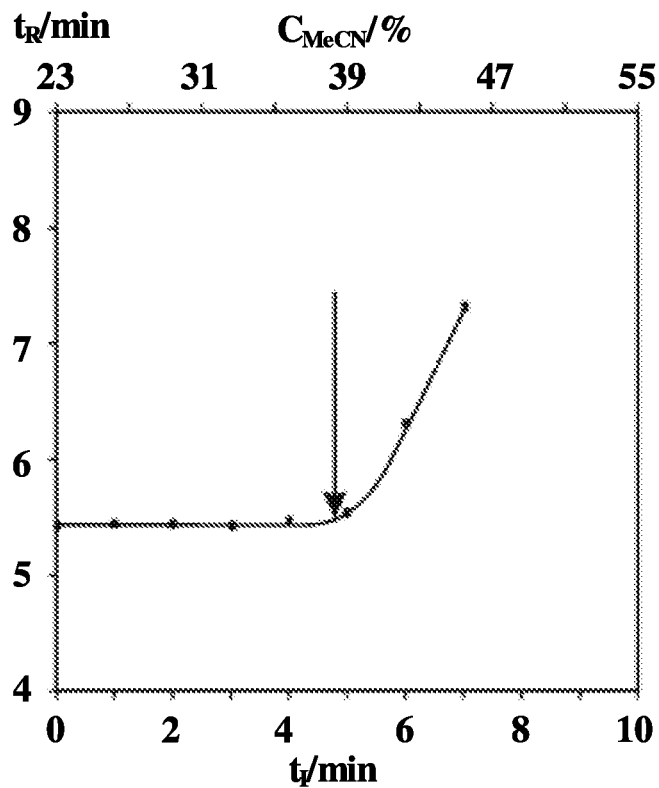
Figure 1F:
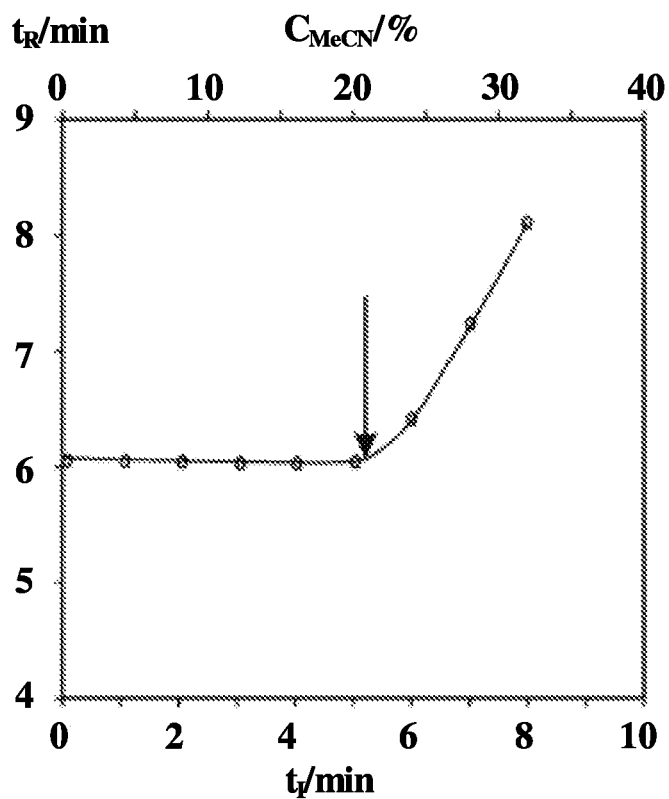

FIG. 1E shows the relationship between retention time $t_R$ and injection time $t_i$ of carbonic anhydrase. To calculate $t_{CMP}$ quantitatively, mark the retention time of the $n_i$ injection as $t_{R,n}$ and the $n_{i-1}$ injection as $t_{R,n-1}$. The average of n−1 different retention time $t_R$, from $t_{R,1}$ to $t_{R,n-1}$, of the different injection time, from the first one to the $n_i$ one, is marked as $t_{Ra}$; standard deviation is $\pm 2\sigma$. If the average standard deviation is larger than $2\sigma$, it indicates that proteins on the chromatographic column undergone significant movement. Based on the above standard, we can determine that the moment protein having significant movement is between $t_{R,n-1}$ to $t_{R,1}$, namely the interval marked by the vertical arrow between two injections in FIG. 1D.

Fitting the data point on the right of the vertical arrow in FIG. 1D, the function using for fitting is:

$$t_R = a + bt_i + ct_i^2 \quad (6)$$

Wherein, a, b, c are constant to be fitted, they are related to the properties of the proteins themselves. Equation (7) is obtained after fitting:

$$t_R = 0.0707 t_i^2 - 1.7985 t_i + 32.652 \quad (7)$$

Wherein, $R^2 = 0.9992$.

It should be noted that in certain circumstances, $t_R$ does not have a mathematically real solution; thus, other types of mathematical equations, such as $\log t_R$ vs. $\log t_i$ or $t_R$ vs $t_i^2$ may be adopted to obtain the solution.

Apply $t_R = t_{Ra} + 2\sigma$ in equation 7, $t_i$ obtained now is the critical migration time $t_{CMP}$.

And then critical migration eluent concentration $C_{CMP}$ can be obtained using equation (8) and equation (9) respectively:

$$C_{CMP} = t_{CMP} \times t_g \quad (8)$$

Wherein, $t_g$ is the linear gradient steepness, namely the eluent concentration change rate in unit time. It can be calculated by:

$$t_g = V\% / t_T \quad (9)$$

Wherein, V % is the eluent concentration changing amount indicated with volume fraction in linear gradient elution, $t_T$ is the linear elution gradient time corresponding to V %. In fact, the injection time of the second dimensional separation is 3-5 minutes earlier than $t_T$, which because that it is suitable for carbonic anhydrase in this specific implements.

Operation Process (1) According to the method mentioned above, make sure the $C_{CMP}$ of the each protein, which need to be retained under the condition of the second or multi-dimension separation, in the protein sample;

(2) According to the knowledge which is well-known by technicians in this field, select mobile phase with suitable composition, turn on the pump A (3), set the suitable gradient elution conditions, including the initial concentration, linear or non-linear gradient elution, gradient time etc. Through the four channel gradient unit 1-2, suitable solvent is removed and transported from the mobile phase tank in a suitable flow rate (For example, solvent 1 and solvent 2 are removed and transported respectively from mobile phase tank 1 and mobile phase tank 2.). And, the separation device is connected to any chromatographic columns or cakes, so that necessary equilibrium is done for the chromatography system.

(3) Sample Injection: six-port valve 4-1 is switched to "load" state (Port 1 and port 6 are connected, port 2 and port 3 are connected and port 4 and port 5 are connected.). Inject some protein sample mixture through port 5 of the six-port valve 4-1 (For example, 100 μL.) and hold the sample in the sample loop. Then, turn the 2D-LC separation system based on this invention to form the flow path B0 state (the first dimensional separation flow path for injection); turn on the pump A (3); through the four channel gradient unit 1-2, suitable solvent is removed and transported from the mobile phase tank in a suitable flow rate, so that samples hold in the sample loop is transferred into the 2D-LC separation system based on this invention. Then, turn the 2D-LC separation system based on this invention to form the flow path B state (the first dimensional separation flow path for non-injection); turn on the pump A (3); through the four channel gradient unit 1-2, suitable solvent is removed and transported from the mobile phase tank in a suitable flow rate (For example, solvent 1 and solvent 2 are removed and transported respectively from mobile phase tank 1 and mobile phase tank 2.) and through six-port valve 6-1 and 6-2, the chromatographic column or cake for first dimensional separation is connected to the flow path. Through gradient elution, protein samples are separated into different fractions with different retention times in the chromatographic column or cake and the fractions are detected in detector 13.

(4) Collect and reserve the intermediate fraction: For fractions need to be separated in the second dimensional chromatography, by switching the eight-port valve 10-1 and 10-2, liquid storage tubing 10-2 is connected with any of the collect-reserve device 10-8, so that this fraction is collected and stored in this collect-reserve device. For fractions need not to be separated in the second dimensional chromatography, by switching the eight-port valve 10-1 and 10-2, liquid collect-reserve device 10-1 is connected, so that this fraction pass through the liquid collect-reserve 10-1 and detector 13 and then, flow out of the system from draining port 17-2. After all the fractions are stored in one liquid collect-reserve device or discharged out of the system, the first dimensional chromatography separation is completed.

(5) The second dimensional separation: Then, turn the 2D-LC separation system based on this invention to form the flow path C state (the second dimensional separation flow path); by switching the eight-port valve 10-1 and 10-2, any of the liquid collect-reserve device storing the intermediate fractions from the first dimensional separation is connected; by switching the six-port valve 6-1 and 6-2, the chromatographic column or cake for the second dimensional separation is connected. Turn on the pump A (3); through the four channel gradient unit 1-2, suitable solvent is removed and transported from the mobile phase tank in a suitable flow rate (For example, solvent 3 is removed and transported from mobile phase tank 3.), so that the intermediate fractions stored in this liquid collect-reserve device flow into mixer 12. At the same, turn on the pump B (9); through the four channel gradient unit 1-1, suitable solvent is removed and transported from the mobile phase tank in a suitable flow rate (For example, solvent 3 and solvent 4 are removed and transported respectively from mobile phase tank 3 and mobile phase tank 4.), so that the intermediate fractions mix with the mobile phase and the injection mixture for the second dimensional separation is obtained. The mixture is injected into the chromatographic column for the second dimensional separation; by adjusting the flow rate of pump A (3), four channel gradient unit 1-1, pump B (3) and four channel gradient unit 1-2, the injection mixture eluent concentration C is lower than the critical migration eluent concentration on which all the intermediate fractions must be retained in the second dimensional separation, so that all these protein is retained in the chromatographic column or cake and the second dimensional injection is completed.

Then, through gradient elution, injection mixture is separated into different fractions in the chromatographic column or cake and the fractions are detected in detector 13. Samples after the second dimensional separation are discharged out of the system from draining port 17-2 and collected into fraction collector.

Repeat this step so that all the fractions need to be separated in the second dimensional separation are separated.

In a specific embodiment, the gradient elution in above step (4) is linear gradient elution.

In a specific implement, the gradient elution in above step (4) is non-linear gradient elution.

According to the properties of the protein mixture to be separated, technicians in this field can select the suitable chromatographic column or cake for separation easily, so does the mobile phase solvent.

Buffer Exchange

Before or after the sample injection in said step (4), when the mobile phase composition of the intermediate fractions after the last dimensional separation doesn't match the mobile phase composition of the next dimensional separation, the mD-LC separation method or two-dimensional liquid chromatography separation method based on this invention can also include the steps as follows:

(1) Buffer exchange: mobile phase using in the second dimensional separation is used as buffer (For example, solvent 3 and solvent 4 reserve in mobile phase tank 3 and mobile phase tank 4.); through pump A (3) and/or pump B (9), this buffer solution is transported into chromatographic column or cake for the second dimensional separation. Wherein, the buffer eluent concentration C is lower or higher than the critical migration eluent concentration on which all the intermediate fractions must be retained in the next dimensional separation, so that at least part of the original mobile phase for the first dimensional separation in the column is replaced (For example, solvent 1 and solvent 2).

(2) If we denote the fraction collected after the previous dimensional separation as mobile phase X (X indicates that the mobile phase composition is known. For different proteins, the composition is different from each other.) and regarded it as buffer, do the same buffer exchange in the same way said above, thus, the second injection and buffer exchange are done at the same time. And then, the second dimensional separation is done for the intermediate fractions.

(3) After the second dimensional sample injection, the mobile phase, for example, mobile phase 2, which helps to push the collection liquid out of the liquid collect-reserve device, mix with mobile 3 or 4 in a suitable ratio, so that the 2D-LC system rebalance is completed.

(4) Chromatographic columns need to be cleaned periodically with strong elution solution. Pump A or B can be used to imbibe any of the solutions from the mobile phase tank to clean it. The columns can be cleaned with suitable in high flow rate.

Multi-Dimensional Liquid Chromatography Separation System

Although the specific implement said above is explained aiming at the 2D-LC separation system and its operation method shown in FIG. 2, it is easy for technicians in this field to develop it into multi-dimensional liquid chromatography separation system.

Technicians in this field can under easily that, compared with the 2D-LC separation system shown in FIG. 2, the multi-dimensional liquid chromatography separation system includes more mobile phase tanks and the infusion device has more liquid transportation pipelines.

According to the knowledge which is well-known in this field, technicians in this field should be able to make appropriate changes for the 2D-LC separation system flow path switching device, so that fractions separated from the second dimension and to be separated in the next dimension do not flow out of the system and are collected and reserved again as intermediate fractions in the liquid collect-reserve device. In the next more dimensional separation, these intermediate fractions are further separated just in the same way as the second dimensional separation mentioned above.

The specific implement for protein sample separation with 2D-LC separation system shown in FIG. 2 is as follows:

Example 1

The 2D-LC (WCX-HIC) separation of seven proteins using commercial Aolan 2D-LC (WCX-HIC) chromatographic column.

According to the two dimensional liquid chromatography separation system and method, this specific embodiment will separate Myoglobin (Myo), Ribonuclease (RNase), Cytochrome C (Cyt-c), -Chymotrypsinogen (-Chy), Lysozyme (Lys), Carbonic Anhydrase (Car) and -Amylase Amy) from these seven proteins mixture. Wherein, the first dimension is weak cation exchange (WCX) separation mode and the second dimension is hydrophobic interaction (HIC) separation mode. Chromatographic column used in this specific embodiment is the commercial Aolan 2D-LC (WCX×HIC) chromatographic column and in fact, the WCX/HIC mixed-mode chromatographic column (150 mm×7.9 mm). In the first WCX separation mode and second HIC separation mod, we both use this chromatographic column.

The separation result is as shown in FIG. 3. The FIG. also shows the concentration versus time curve. Separation is done according to the 2D-LC separation process mentioned foregoing:

In the first dimensional WCX mode separation, pump 1 is used to transport the mobile phase and do the gradient elution for the WCX mode. Myo, Rnase A and Lys are completely separated (peak 1, 2, 5 in the FIG. 3 left); Car and α-Amy cannot retain (peak 6, 7, in the FIG. 3 left); Cyt-c and -Chy cannot be completely separated (peak 3, 4, in the FIG. 3 left). Therefore, after the first dimensional separation, protein Myo, Rnase and Lys can be obtained. Intermediate fractions containing Car and Amy and intermediate fractions containing Cyt-c and α-Chy are collected respectively in the liquid storage tubing 10-2 and 10-3 of the collect-reserve device.

After the first dimensional separation, increase the salt concentration; do the second dimensional injection, buffer exchange; at the same time, carry out the re-equilibrium of the second dimensional HIC separation system according to the method mentioned foregoing (the salt concentration platform area, as shown in FIG. 3). The method is that, pump B (9) is used to transport mobile phase A for HIC to mixer 12. By adjusting the liquid flow rate of pump A (3) and pump B (9), the concentration after mixing is lower than the critical migration eluent concentration $C_{CMP}$ of Cyt-c and α-Chy (This $C_{CMP}$ has been calculated accurately and it is obtained in advanced through the conventional liquid chromatography analysis shown in FIG. 1). After the second dimensional injection, buffer exchange and second dimensional separation system re-equilibrium, intermediate fraction Cyt-c and -Chy is retained totally in one chromatographic column. Then, through the next dimensional HIC mode gradient elution, Cyt-c and -Chy are completely separated (peak 3', 4' in the FIG. 3).

According to the method mentioned foregoing, re-inject the intermediate fraction containing Car and -Amy; do the buffer exchange, the third time system re-equilibrium (It is the second time HIC separation.). The manner is: pump B (9) is used to transport mobile phase A for HIC to mixer 12. By adjusting the liquid flow rate of pump A (3) and pump B (9), the concentration after mixing is lower than the critical migration eluent concentration $C_{CMP}$ of Car and -Amy (This $C_{CMP}$ has been calculated accurately and it is obtained in advanced through the conventional liquid chromatography analysis shown in FIG. 1.). After the three process mentioned above, intermediate fraction Car and -Amy is retained totally in one chromatographic column. Then, through the next dimensional HIC mode gradient elution, Car and -Amy are completely separated (peak 6', 7' in the FIG. 3).

As mentioned above, using the liquid chromatography separation system based on this invention, the complete separation of the 7 proteins mentioned above is completed in 80 min.

The chromatographic column, mobile phase and chromatographic conditions are as follows:

Chromatographic column: Aolan 2D-LC (WCX×HIC) chromatographic column and in fact is a WCX/HIC mixed-mode chromatographic column (150 mm×7.9 mm) HIC mobile phase: solution A: 20 mmol/L $KH_2PO_4$+3.0 mol/L $(NH_4)_2SO_4$ (pH=6.5); solution B: 20 mmol/L $KH_2PO_4$ (pH=6.5);

WCX mobile phase: solution A: 10 mmol/L $KH_2PO_4$ (pH=6.5); solution B: 10 mmol/L $KH_2PO_4$+1 mol/L NaCl (pH=6.5);

Chromatographic Conditions:
0-15 min: 100% A-80% A (20% B), 2.0 mL/min;
15-20 min: 80% A (20% B)-50% A (50% B);
20-25 min: 50% A (50% B);
25-28 min: 100% C, 4.0 mL/min;
28-33 min: 100% C, 1.0 mL/min+mixing pump: 100% C, 3.0 mL/min;
33-53 min: 100% C-100% D, 2.0 mL/min;
53-56 min: 100% C, 4.0 mL/min;
56-61 min: 100% C, 1.0 mL/min+mixing pump: 100% C, 3.0 mL/min;
61-81 min: 100% C-100% D, 2.0 mL/min;
81 min to the end: 100% D.

Example 2

The three dimensional (WCX×HIC×SEC) purification and desalination of two proteins α-Chymotrypsin and Trypsin, using the commercial Shim-pack PA-CM 2D-LC WCX chromatographic column and commercial TSKgel G4000SW$_{XL}$ SEC chromatographic column.

According to the two 2D-LC separation system and method, this specific embodiment will purify α-Chymotrypsin (-Chy) and Trypsin (Try) from the degreased bovine pancreas extract which is prepared in conventional methods at the same time. And then, for the separated proteins, desalinate respectively. Wherein, the first dimension is weak cation exchange (WCX) separation mode and the second dimension is hydrophobic interaction (HIC) separation mode. Because of the large amount of liquid from the second dimension and the constant change of protein concentration, what's more, collected liquid cannot be injected into the SEC column once, it must be collected into oval liquid collection tubing and mixed through oscillator stirring. And then, it is injected respectively into the third dimensional SEC column for desalination. The separation result is as shown in FIG. 4. The figure also shows the concentration versus time curve. Separation is done according to the 2D-LC separation process mentioned foregoing:

In the first dimensional WCX mode separation, pump A (3) is used to transport the mobile phase and do the gradient elution for the WCX mode, so that α-Chy and Try are separated initially (peak 1, 2 in the FIG. 4). However, purity after initial separation is for less than requirement, therefore, after the initial separation, intermediate fractions containing α-Chy and Try are collected respectively in the liquid storage tubing 10-2 and 10-3 of the collect-reserve device.

After the first dimensional separation, according to the method mentioned forgoing, intermediate fractions containing α-Chy (2) and Try (1) are collected respectively into two liquid collect-reserve devices (peak Try (1) and α-Chy (2) in FIG. 3). According to the method mentioned forgoing, re-inject α-Chy (2); do the buffer exchange; at the same time, make the re-equilibrium of the second dimensional HIC separation system (the salt concentration platform area, as shown in FIG. 4). The method is that, pump B (9) is used to transport mobile phase A for HIC to mixer 12. By adjusting the liquid flow rate of pump A (3) And pump B (9), the concentration after mixing is lower than the critical migration eluent concentration $C_{CMP}$ of α-Chy (This $C_{CMP}$ has been calculated accurately and it is obtained in advanced through the conventional liquid chromatography analysis shown in FIG. 1.). After the second dimensional injection, buffer exchange and second dimensional separation system re-equilibrium, intermediate fraction α-Chy is retained totally in one chromatographic column. Then, through the next dimensional HIC mode gradient elution, purified α-Chy (2') is obtained.

According to the method as described above, re-inject Try (1); do the buffer exchange; at the same time, complete the re-equilibrium of the second dimensional HIC separation system (the salt concentration platform area, as shown in FIG. 4). The method is that, pump B (9) is used to transport mobile phase A for HIC to mixer 12. By adjusting the liquid flow rate of pump A (3) And pump B (9), the concentration after mixing is lower than the critical migration eluent concentration $C_{CMP}$ of Try (This $C_{CMP}$ has been calculated accurately and it is obtained in advanced through the conventional liquid chromatography analysis shown in FIG. 1.). After the second dimensional injection, buffer exchange and second dimensional separation system re-equilibrium, intermediate fraction Try (1) is retained totally in one chromatographic column. Then, through the next dimensional HIC mode gradient elution, purified Try (1') is obtained.

Collect the α-Chy and Trypsin after second dimensional purification into respectively oval-shape liquid collect-reserve tub; oscillate the liquid for 5 min so that the collected mix good; inject the mixture respectively into the commercial TSKgel G4000SW$_{XL}$ SEC chromatographic column for desalination.

As mentioned above, using the liquid chromatography separation system based on this invention, the separation and purification of α-Chymotrypsin and Trypsin is completed in 70 min. The purity can respectively be 82% and 95%; the total mass recovery ratio can respectively be 85.0% and 83.5%; the activity recovery ratio can respectively be 59.4% and 76.5%. Because of the on-line collection, storage, re-injection and desalination, compared with the mass and activity ratio 50-70% after offline desalination, the mass and activity ratio of the two proteins improve greatly to 80-90% after online desalination.

Non-linear gradient elution is used in the separation, wherein, the chromatographic column, mobile phase and chromatographic conditions are as follows:

WCX chromatographic column: the commercial Shim-pack PA-CM (100 mm×7.5 mm I.D);

WCX mobile phase: solution A: 0.02 mol/L Tris (hydroxymethyl) aminomethane (Tris-HCl, pH=6.5); solution B: 0.02 mol/L Tris-HCl+1 mol/L NaCl (pH=6.5);

HIC mobile phase: solution C: 0.05 mol/L KH$_2$PO$_4$+3.0 mol/L (NH$_4$)$_2$SO$_4$ (pH=7.0); solution B: 0.05 mol/L KH$_2$PO$_4$ (pH=7.0).

SEC chromatographic column: TSKgel G4000SW$_{XL}$ (300×7.8 mm I.D);

SEC mobile phase: 0.02 mol/L NaCl. Flow rate: 1.0 mL/min.

Chromatographic Conditions:

0-20 min: 100% A-50% A (50% B), 1.0 mL/min;
20-25 min: 50% C (50% D), 3.0 mL/min;
25-30 min: 50% C (50% D), 1.0 mL/min+100% C, 1.0 mL/min;
30-40 min: 50% C (50% D)-100% D, 1.0 mL/min;
40-45 min: 50% C (50% D), 3.0 mL/min;
45-50 min: 50% C (50% D), 1.0 mL/min+100% C, 1.0 mL/min;
50-60 min: 50% C (50% D)-100% D, 1.0 mL/min;
60-65 min: 100% D to the end.

Injection amount: -Chy 10 μL, Trypsin 20 μL. The protein concentration of Trypsin and α-Chy is both 10 mg/mL.

Example 3

The rapid separation and purification of Cytochrome C (Cyt-c) in bovine pancreas with online 1C-2D-LC (2D, WCX-HIC).

First, extract crudely Cyt-C from bovine pancreas: Remove fat and connective tissue and then clean the fresh bovine pancreas; store it in −20° C. fridge immediately; take frozen bovine pancreas out of the fridge and make it into pieces, mince it using meat mixer, and then, add 2 folds volume of sulfuric acidulated water (pH=4) and extract under stirring. Use 1 mol/L H$_2$SO$_4$ to adjust pH every 3 hours so that the pH is kept at 3.5-4.0. Extract with stirring for more than 12 hours at low temperature (4° C.); Use 1 mol/L H$_2$SO$_4$ to adjust pH to 6.5, use four layers gauze to filtrate the extracting solution and collect filtrate, keep in place at 4° C.; at last, centrifuges the extracting solution at 10,000 rpm for 20 min and the collected supernatant fluid is the Cyt-C crude extracting solution. All the operations are done at 4° C., filtrate is stored in −20° C. fridge for further use.

The chromatographic method using in this specific embodiment is that, as shown in FIG. 5, in the first dimensional chromatography separation, under the condition that mobile phase flow rate is 1.0 mL/min and NaCl linear gradient elution flow rate is 0 to 1.0 mol/L, in the interval 5.5-10.5 min, the first dimensional Cyt-c sample is collected on-line and stored in the collect-reserve device. Then, use the large flow rate 2.5 mL/min to approach equilibrium the chromatography system rapidly with 3.0 mol/L ammonium sulfate. Then, just the same first and second dimensional chromatography method as shown in specific embodiment 2, discharge the first dimensional collected liquid from the collect-reserve device with a flow rate of 1.0 mL/min and at the same time, mix it with the 3.0 mol/L ammonium sulfate, transported by pump B with a flow rate of 2.0 mL/min, in the chromatographic mixer. Now, the salt concentration of the first dimensional collected liquid is increased from very low to 2.0 mol/L, so that its retention capacity is strong enough on the same 2D (WCX,HIC) column, under the condition of HIC separation mode. This process is completed in 7.0 min. Finally, do the 10 min linear gradient elution for the retained protein with 3.0 mol/L ammonium sulfate and collect the fractions in time interval 43.5-46.5 min.

Pump B (9) is used to transport mobile phase A for HIC to mixer 12. By adjusting the liquid flow rate of pump A (3) And pump B (9), the concentration after mixing is lower than the critical migration eluent concentration $C_{CMP}$ of Cyt-c and α-Chy (this $C_{CMP}$ has been calculated accurately and it is obtained in advanced through the conventional liquid chromatography analysis shown in FIG. 1.). After the second dimensional injection, buffer exchange and second dimensional separation system re-equilibrium, intermediate fraction Cyt-c and α-Chy is retained totally in one chromatographic column. Then, through the next dimensional HIC mode gradient elution, Cyt-c and α-Chy are separated (peak 3', 4' in the FIG. 3).

The chromatographic column, mobile phase and chromatographic conditions are as follows:

Chromatographic column: the Xi' an Aolan-2D (WCX-HIC) chromatographic column (silica-base, particle diameter: 5 μm; pore size: 30 nm; 50 mm×4.6 mm I.D).

Deal with the Cyt-C which is separated and collected respectively from the bovine pancreas, WCX as the first dimension and HIC as the second dimension. And then, Tab. 1 shows the purity of Cyt-C in each electrophoresis band after purity scan.

TABLE 1 the electrophoresis thin layer scanning data of bovine pancreas Cyt-C separation and purification

| Electrophoresis Band | Name | Cyt-C purity(%) |
| --- | --- | --- |
| 1 | Cyt-C in bovine pancreas original sample | 2.5 |
| 2 | IEC one dimensional separation result | 56.7 |
| 3 | HIC one dimensional separation result | 62.6 |
| 4 | IEC-HIC two dimensional separation result | 95.7 |
| 5 | Standard Cyt-C electrophoresis band | 97.5 |

To confirm the result of IEC-HIC two dimensional liquid chromatography separation, RPLC is used to test and analysis the Cyt-C purity collected from the IEC-HIC two dimensional liquid chromatography separations. The calculated purity is more than 97%.

```
                        SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Fully synthetic

<400> SEQUENCE: 1

Gly Glu Pro Pro Pro Gly Lys Pro Ala Asp Asp Ala Gly Leu Val
1               5                   10                  15
```

IEC mobile phase: solution 1: 20 mmol/L $KH_2PO_4$ (pH=6.5); solution 2: 20 mmol/L $KH_2PO_4$+1 mol/L NaCl (pH=6.5);

HIC mobile phase: solution 3: 20 mmol/L $KH_2PO_4$+3.0 mol/L $(NH_4)_2SO_4$ (pH=6.5); solution 4: 20 mmol/L $KH_2PO_4$ (pH=6.5);

Non-linear gradient elution mode (dotted line shown in FIG. 5)

Chromatographic Conditions:
0-20 min: 100% 1-100% 2, 1.0 mL/min;
20-30 min: 100% 3, 2.5 mL/min;
30-37 min: pump A: 100% 1, 1.0 mL/min+pump B 100% 3, 2.0 mL/min;
37-47 min: 100% 3-100% 4, 1.0 mL/min;
47-52 min: 100% 4.

The invention claimed is:

1. A multidimensional liquid chromatography separation system for protein separation, the multidimensional liquid chromatography separation system comprising a detection device, a mobile phase tank, a first infusion device, a second infusion device, a first injector device, a second injector device, a separation device, a collect-reserve device comprising at least one sample loop, at least two draining devices, and a flow path switching device, wherein:
   the mobile phase tank is used for the storage of mobile phase for the multidimensional liquid chromatography separation;
   the first and second infusion devices are employed independently to take out mobile phase which is suitable for the liquid chromatography separation from the mobile phase tank and then, the mobile phase is transported to the multidimensional liquid chromatography separation system; and the first infusion device and the second infusion device measure and adjust the flow rate of the mobile phase independently; in the first dimensional separation, the first infusion device is used to transport mobile phase suitable for the first dimensional separation to the first injector device; in the second dimension or a higher dimensional separation, the first infusion device is used to transport mobile phase suitable for the second dimensional or the higher dimensional separation to the collect-reserve device and push the intermediate fraction stored in the collect-reserve device into the second injector device; at the same time, the second infusion device takes out mobile phase suitable for the second dimensional or higher dimensional separation from the mobile phase tank and then, transport it to the second sample injection device;

the first injection device introduces original samples from outside of the system and pushes the original samples into the separation device together with mobile phase from the first infusion device; the second injector device includes a sample mixer; said sample mixer is used to mix the previous fraction from at least one sample loop and mobile phase from the collect-reserve device and mobile phase from the second infusion device, so that a sample mixture is obtained, and then, the sample mixture is pushed into a next dimensional separation device;

the separation device includes a chromatographic column switching unit and a total number, "n" chromatographic columns, or a chromatographic column with a total number of separation modes "m", and liquid in the separation device is separated into different fractions through the chromatographic column, in which the chromatographic column selector helps to put the liquid in the separation device selectively into one of the chromatographic column of the "n" chromatographic columns; "n" is a nonnegative integer and "m" is the number of different separation modes used in the multidimensional liquid chromatography separation system, and "n" and "m" need to satisfy:

$$m \geq n \quad (1)$$

$$m = q \times (i-1) \quad (2)$$

wherein "i" is a positive integer; "q" stands for the number of chromatographic columns having the number "i" of separation modes;

the collect-reserve device includes the number "p" of the sample loops switching units and "p" is greater than or equal to 1; the sample loops switching unit is used to control the direction of liquid movement in the collection and collect-reserve device to selectively pass through at least one of the collect-reserve devices and then, the collect-reserve device is employed to collect the intermediate fraction that has been separated and required to do subsequent separation by other separation mode, and the second fraction containing the target protein is also stored in at least one of the collect-reserve devices;

said at least two draining devices push the liquid in the flow path out of the system;

the flow path switching device is made up from valves connected to the device and pipes above by switching the valves of the flow path switching device, it provides not only the flow path for conventional liquid chromatography separation but also the flow path for multidimensional liquid chromatography separation; and the first infusion device and the second infusion device adjust and measure the flow rate of mobile phase for the second or higher dimensional separation and adjust an eluent concentration of the sample mixture in the second or higher dimensional separation to be lower than a critical migration eluent concentration $C_{CMP}$, wherein target protein in the sample mixture remains within a chromatographic column in the second or higher dimensional separation when the eluent concentration of the sample mixture is lower than the critical migration eluent concentration $C_{CMP}$.

2. The multidimensional liquid chromatography separation system for protein separation of claim 1, wherein the next dimensional separation device is a separation device having mixed separation mode, or having a single mode to be different from the separation mode of the previous dimension.

3. The multidimensional liquid chromatography separation system for protein separation of claim 1, wherein the first infusion device and the second infusion device have multivariate gradient units and pumps, respectively; and the multivariate gradient units have multiple infusion channels and can transport and measure the flow rate of any channel.

4. The multidimensional liquid chromatography separation system for protein separation of claim 1, wherein the multidimensional liquid chromatography system is made as integrate-type; namely all hardwares are assembled inside a shell and all operations are controlled by one control system, or the multidimensional liquid chromatography system is made as separate-type, namely each of hardware and automatic control systems is assembled in two or more shells and operated using the automatic control system of a conventional liquid chromatograph or other automatic control systems.

5. The multidimensional liquid chromatography separation system for protein separation of claim 1, wherein the injection mixer of the second injection device is mixing tank or pipe mixer.

6. The multidimensional liquid chromatography separation system for protein separation of claim 1, wherein the valves are positioned on the pipe line connecting the second sampling device and the second infusion device, the valves are used to control whether the second sample injection device and the second infusion device are connected or not.

7. The multidimensional liquid chromatography separation system for protein separation of claim 1, wherein at least one multi-ported valve is inserted in the chromatographic column switching unit, and the multi-ported valve has an inlet as the inlet of the separation device and n valve outlets connecting with the n chromatographic columns one-by-one, the multi-ported valve is used to transport the liquid in the separation device selectively into one of the chromatographic columns by switching the n valve outlets.

8. The multidimensional liquid chromatography separation system for protein separation of claim 1, wherein a desalination device is inserted in multidimensional liquid chromatography separation system, said desalination device is used to remove at least part of the salt from the liquid.

9. The multidimensional liquid chromatography separation system for protein separation of claim 1, wherein the geometric volume of the sample loops are different or partially different from each other.

10. The multidimensional liquid chromatography separation system for protein separation of claim 1, wherein the sample loop switching unit in the collect-reserve device includes a third and a fourth multi-ported valve.

11. The multidimensional liquid chromatography separation system for protein separation of claim 10, wherein liquid is allowed to pass reversely through the third and fourth multi-ported valve.

12. The multidimensional liquid chromatography separation system for protein separation of claim 1, wherein the flow path switching device constitutes any kind of the following flow path selectively to switch flow path:
   conventional separation flow path, which connects in turn the mobile phase tank, the first infusion device, the first injector device, the separation device, the detection device and the first draining device in this flow path;
   a first dimensional separation flow path, which connects in turn the mobile phase tank, first infusion device, separation device, detection device, the collect-reserve device and second draining device in this flow path;
   a second or higher dimensional separation flow path for intermediate fraction collection, which connects in turn the mobile phase tank, first infusion device, collect-reserve device, second injector device, separation device, detection device and first draining device; and connects in turn the mobile phase tank, second infusion devices and second injection device in this flow path; and
   a second or higher dimension separation flow path without collecting intermediate fraction, which connects in turn the mobile phase tank, the first infusion device, collection and storage device, second injector device, separation device, detection device and first draining device, and connects in turn the mobile phase tank, second infusion device and second injection device in this flow path.

13. The multidimensional liquid chromatography separation system for protein separation of claim 1, wherein it includes a constant temperature device, which keeps at least the collect-reserve device remain constant temperature, at which temperature the inactivation time of proteins can be extended.

14. The multidimensional liquid chromatography separation system for protein separation of claim 1, wherein it includes a sterilization device, which can at least kill bacterium in the collect-reserve device fully or partially.

15. The multidimensional liquid chromatography separation system of claim 1, further comprising an automatic control device, wherein:
   the automatic control device controls the separation device, the collect-reserve device, and the flow path switching device.

16. A two-dimensional liquid chromatography separation system for protein separation, comprising detection device, wherein the two-dimensional liquid chromatography separation system includes mobile phase tank, a first infusion device and second infusion device, a first injection device and second sample device, separation device, collect-reserve device comprising at least one sample loop, at least one draining device and flow path switching device, in which:
   1) the mobile phase tank is used for the storage of mobile phase for the two-dimensional liquid chromatography separation;
   2) the first and second infusion devices are employed independently to take out mobile phase which is suitable for the liquid chromatography separation from the mobile phase tank and then, the mobile phase is transported to the two-dimensional liquid chromatography separation system; and they measure and adjust their flow rate independently; in the first dimensional separation, the first infusion device is used to transport mobile phase suitable for the first dimensional separation to the first injector device; in the second dimensional separation, the first infusion device is used to transport mobile phase suitable for the second dimensional separation to the collect-reserve device and push the intermediate fraction stored in the at least one collect-reserve device into the second injector device, the second infusion device takes out mobile phase suitable for the second dimensional separation from the mobile phase tanks and then, transport it to the second sample injection device;
   3) the first injection device introduces samples to be separated which includes proteins to be separated from outside the system, and pushes them into the separation device together with mobile phase from the first infusion device; the second sample injection device includes sample mixer, the sample mixer is used to mix the intermediate fraction from at least one sample loop and mobile phase from the collect-reserve device and mobile phase from the second infusion device, so that a sample mixture is obtained, and then, the sample mixture is pushed into said separation device;
   4) said separation device includes chromatographic column switching unit and a total number, "n" chromatographic columns, or a chromatographic column with a total number of separation modes "m", and liquid in the separation device is separated into different fractions through the chromatographic column, in which the chromatographic column selector helps to put the liquid in the separation device selectively into one of the chromatographic column of the "n" chromatographic columns; "n" is a nonnegative integer and "m" is the number of different separation modes used in the two-dimensional liquid chromatography separation system, and "n" and "m" need to satisfy:

$$m \geq 2 \qquad (3)$$

5) the collect-reserve device includes the number "p" of the sample loops and sample loops switching units, and "p" is greater than or equal to 2; the sample loops switching unit is used to control the direction of liquid movement in the collection and collect-reserve device to selectively pass through at least one of the collect-reserve devices and then, the collect-reserve device is employed to collect the intermediate fraction that has been separated and required to do subsequent separation by other separation mode, and the second fraction containing the target protein is also stored in at least one of the collect-reserve devices;
   6) said at least two draining devices push the liquid in the flow path out of the system; and
   7) the flow path switching device is made up from valves connected to the device and pipes above by switching the valves of the flow path switching device, it provides not only the flow path for conventional liquid chromatography separation but also the flow path for two-dimensional liquid chromatography separation; and
   the first infusion device and the second infusion device adjust and measure the flow rate of mobile phase they transport for the second dimensional separation and adjust the eluent concentration of the injection mixture in the second dimensional separation to be lower than the critical migration eluent concentration $C_{CMP}$, wherein target protein in the target intermediate fractions remains within a chromatographic column in the second dimensional separation when the eluent concentration of the injection mixture is lower than the critical migration eluent concentration $C_{CMP}$.

17. A multidimensional liquid chromatography separation method for protein separation using the multidimensional liquid chromatography separation system of claim 1, comprising:
1) preparation in advance: determining the critical migration eluent concentration $C_{CMP}$ under the condition of the second dimension or a higher dimensional separation that the target proteins in the protein samples to be separated are retained;
2) the first dimensional separation: separating the protein samples through the gradient elution on conventional liquid chromatography separation, thereby obtaining different fractions;
3) collection and storage of the intermediate fraction: collecting and storing the intermediate fraction of the fractions after the last dimensional separation, which need to be further separated;
4) the second dimensional or multidimensional separation: mixing all or part of the intermediate fraction to be separated in next dimension and mobile phase using in the next dimension together so that injection mixer is acquired, and then, the injection mixer being injected into the chromatographic column using in the next dimensional separation, then through the gradient elution, as mentioned in step 4), the injection mixer retained in the chromatographic column using in the next dimensional separation being separated in the second dimension or a higher dimensional liquid chromatography and once again, thereby obtaining the different fractions; and for all intermediate fractions that obtained from the previous dimension and to be separated in the next dimension, such separation being done;
5) repeating the above steps 3) and 4), so as to obtain all of the target protein products;
wherein in the step 4), the flow rate of mobile phase for the second or higher dimensional separation is adjusted and measured so that the eluent concentration of the injection mixture is lower than the critical migration eluent concentration $C_{CMP}$ on which all or part of the target protein in the target intermediate fractions must be retained in the second or higher dimensional separation.

18. The method of claim 17, wherein in the step 4), the intermediate fraction is injected into the chromatographic column through the high velocity mobile phase.

19. The method of claim 17, wherein in the step 4), before or after injection, the following buffer exchange steps are further included:
mobile phase which will be used in the next dimensional separation is used as the buffer, and the buffer is allowed to flow through the chromatographic column used in the next dimensional separation; wherein the eluent concentration of the mobile phase is lower than the critical migration eluent concentration $C_{CMP}$ on which all the target protein in the target intermediate fractions must be retained in the next dimensional separation so that the original mobile phase in the chromatographic column is at least partly replaced.

20. The method of claim 17, wherein the buffer velocity is higher than that usually used in the liquid chromatography separation through the gradient elution.

* * * * *